United States Patent
Rubin et al.

(12)

(10) Patent No.: US 6,319,704 B1
(45) Date of Patent: *Nov. 20, 2001

(54) KUZ, A NOVEL FAMILY OF METALLOPROTEASES

(75) Inventors: Gerald M. Rubin; Duojia Pan, both of Berkeley, CA (US); Jenny Rooke, New Haven, CT (US); Reza Yavari, New Haven, CT (US); Tian Xu, New Haven, CT (US)

(73) Assignees: The Regents of the University of California, Oakland, CA (US); Yale University, New Haven, CT (US)

( * ) Notice: Subject to any disclaimer, the term of this patent is extended or adjusted under 35 U.S.C. 154(b) by 21 days.

This patent is subject to a terminal disclaimer.

(21) Appl. No.: 09/709,126

(22) Filed: Nov. 8, 2000

Related U.S. Application Data

(62) Division of application No. 09/285,502, filed on Apr. 2, 1999, now Pat. No. 6,190,876, which is a division of application No. 08/937,931, filed on Aug. 27, 1997, now Pat. No. 5,935,792

(60) Provisional application No. 60/019,390, filed on Aug. 29, 1996, and provisional application No. 60/053,476, filed on Jul. 23, 1997.

(51) Int. Cl.[7] .............................. C12N 1/21; C12N 9/50; C12N 15/52; C12N 5/10; C07H 21/04

(52) U.S. Cl. ....................... 435/252.3; 435/212; 435/226; 435/320.1; 435/325; 435/348; 536/23.2

(58) Field of Search ................................. 435/252.3, 325, 435/348, 320.1, 212, 226; 536/23.2

(56) References Cited

PUBLICATIONS

Hillier et al. Oct. 24, 1995. The WasU–Merck EST Project. EST–STS accession H69389.

Hillier et al. Mar. 15, 1997. The WasU–Merck EST Project. EST–STS accession T79341.

Pan et al. Kuzbanian controls proteolytic processing of Notch and mediates lateral inhibition during Drosophila and vertebrate neurogenesis. Cell. Jul. 25, 1997, vol. 90 pp. 271–280.

Yedvobnick. Snake venom, fertilization and neurogenesis. TINS. Dec. 1996, vol. 19, No. 12, pp. 528–530.

Wilson et al. 2.2 Mb of contiguous nucleotides sequence from chromosome III of C. elegans Nature Mar. 3,1994, vol. 368 pp. 32–38.

Howard et al. (Jul. 1, 1996) Biochem. J., vol. 317, pp. 45–50.

Howard et al. (Jul. 21, 1995) rat disintegrin–metalloprotease precursor. (Database pir51, accession S52477).

Howard et al. (Jul. 21, 1995) rat disintegrin–metalloprotease. (Database pir51, accession S52920).

*Primary Examiner*—Elizabeth Slobodyansky
(74) *Attorney, Agent, or Firm*—Richard Aron Osman

(57) ABSTRACT

Members of a novel family of polypeptides, the KUZ family, are metalloproteases involved in neuronal partitioning and neuronal development. The invention provides KUZ poylpeptides, antibodies that bind the KUZ polypeptides, KUZ encoding nucleic acids, methods for identifying cells expressing the KUZ polypeptides, methods of identifying ligands that bind to the subject proteins and methods of blocking KUZ polypeptide/ligand interactions

14 Claims, 4 Drawing Sheets

FIGURE 1A

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
      (A) LENGTH: 5630 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
GTTTAAAAAA AACCACCAAG CGAGTTGGAC GCGTAACTCT TTGTAACGGA TCTCGGAACG      60
```

-continued

```
CCGTGGGAGT CGGAAAATCG CTGGACGCGT GTTCGTGCGT TTGCATGTGT GCGTGCGTTC    120
GTGTGTGTGT GTGTGCTAAT GTGCGAGCGG GTGAGCGAAT AAAAATAAAT ATATATCGTC    180
AAGTCAGGCT TAAGAAATGT GCGCTAATCA AAGAAAATGC CCCCAATTCT GGCCAATTGA    240
GAATTGTGGC TAAACAAAAA ATTCGACCGG AGTTCAAAAA TAAACAATCC AGTGAATAAA    300
CACACAAAAT CAATCAAAAA AGAAGATTTT TCTTTTTTAT TTTCGCTTTT AATTTATTAA    360
CGAGAATAAT AAATAAATAA ATAAATAAAT ATAAACAAAA ATAAAAATAT AAGAAAAGTG    420
TACGTGACAA GAGCTCGAAA AGAAGTTGCA ACAAATAGCA AAAATAATTC GTGCGTGCGA    480
AAAAGTGCTG CGAAGTTTTA TGGCCCATGC AAAAAGTGCT AAATTTGTAA ATGGCATGGA    540
AAGTGCAAAG CTCTGATTAA AAAACCCGCG AAGATTGGAG TGCGAGGTGC CGCCCAATAA    600
CGCAACCAAC TACTGCCACA AGGAAATTAT TAAGACCAAT CAACGACCAA AAAAATAAAA    660
AATAAAACAA AAGCAAGCAG AAATTTGGTG CTAGTTCTGT TTAGTCGACA GCCATCCACG    720
TTGGATCCCC ATCGCAAATA ATGTCATCAA AATGTGCTTT CAACATTGTA TTCGTATCGA    780
TCATTTTCAT CATCATCGTA AATGGTTACG CAAAAGATAT TTCTGGAGTT AAAAGAGGTC    840
ATGAACGACT TAACGAATAC ATATCCCACT ATGAAACACT CAACTATGAT CACGAGCACA    900
TCCGAGCTAG TCACAATAGA GCGCGACGAT CAGTGACCAA AGATCAATAT GTACATTTAA    960
AGTTTGCATC ACATGGAAGA GACTTCCATC TTAGATTAAA ACGTGATTTA AATACATTTA   1020
GCAATAAGTT AGACTTTTAT GATAGCAAAG GTCCCATTGA TGTCTCCACG GATCATATCT   1080
ATGAGGGCGA AGTGATAGGG GATCGTAATA GTTATGTATT TGGTTCCATA CACAATGGGG   1140
TATTCGAGGG TAAAATTATA ACGGAACGTG ATGCCTATTA TGTTGAACAT GCCAAACATT   1200
ATTTTCCCAC AAATCGCACG GCGACAACAA CACCACCATC GACTTCGACG ACATCCTCAG   1260
CAACAACAGT CACAAAAAGC ACACAACCAA CACGGCCTTT GGCCAAAAGC AACACCAGTA   1320
CTACTGCCGT TAATAGTAAG ACAGAAAACT TTATAAAGAA AATTGCTGAA TCCACAACGA   1380
CGAGCCAGCA GCTTCCAGAA TATACCGAAT CGTCGTCGTC GTCGTCGACA ACAACATTCC   1440
CACCCACAAC AGAGTATTTC GAGGACGAAA AGGAGCGTAA TGCCGAGGAC GAACTTGATT   1500
TTCACTCCAT TATCTACAAG GAGTCACATG TCGAGGACGC CTACGAAAAT GTGCGCGAAG   1560
GTCACGTGGC CGGCTGTGGC ATCACGGATG AGGTCTCTCA GTGGATGGAG AACATACAAA   1620
ATTCAGCCGT CGAAGAGTTG CCGGAGCCCA TGTCAAAGGA CTATCAAAAG CTCCACCGGA   1680
AGCAGCTGCA CAAAAAGTCC GCCCCACAGC AACAACAGCA GCCCCATCCG CCGAAGAAGT   1740
ACATCAGCGG GGATGAGGAC TTCAAGTATC CCCACCAGAA GTACACGAAG GAAGCTAACT   1800
TCGCCGAGGG TGCATTCTAC GATCCATCGA CCGGACGTCG CCTGGGCTCA TCCGCCAACG   1860
TGGCCGACTG GCATCAGCTC GTCCACGAGC GCGTCCGCCG CGCCACCGAC AATGGTGCTG   1920
GGGATAGGGG CTCATCCGGT GGATCTGGAC GCGGTCGCGA GGACAACAAG AATACCTGCT   1980
CGCTCTACAT TCAAACGGAT CCATTGATAT GGCGCCACAT ACGCGAAGGC ATTGCTGACC   2040
ACGATCGTGG ACGCAAGTAC GAGGTGGATG AGAAAACGCG CGAGGAAATC ACATCGTTGA   2100
TTGCACATCA CGTGACGGCC GTTAATTACA TTTACCGCAA CACAAAGTTC GACGGACGCA   2160
CCGAGCATCG CAACATACGC TTTGAGGTGC AACGCATTAA GATCGATGAC GATTCGGCCT   2220
GTCGCAATTC CTACAATGGT CCACACAATG CCTTTTGCAA TGAACACATG GATGTCTCGA   2280
ACTTTTTGAA TCTGCATTCC CTAGAAGATC ACTCGGACTT TGTTTGGCT TACGTGTTCA   2340
CCTACAGAGA TTTCACTGGC GGCACTTTGG GTCTGGCCTG GGTGGCCAGT GCGTCGGGAG   2400
CCTCTGGTGG AATTTGCGAG AAGTACAAGA CGTACACGGA AACGGTGGGT GGACAGTACC   2460
```

-continued

```
AGAGCACCAA GCGATCACTC AACACGGGCA TCATCACCTT TGTCAACTAC AACAGTCGGG   2520

TGCCGCCGAA AGTGTCGCAG CTTACGTTGG CACACGAGAT TGGCCACAAC TTTGGATCAC   2580

CTCACGATTA CCCTCAGGAA TGTCGTCCTG GTGGCCTAAA TGGCAATTAC ATTATGTTCG   2640

CCAGTGCCAC CTCCGGTGAT AGGCCAAATA ACTCCAAGTT CTCGCCCTGC TCCATTCGGA   2700

ACATCTCCAA TGTCCTTGAC GTGCTGGTGG CAACACGAA GCGCGACTGC TTCAAGGCCT    2760

CGGAAGGTGC CTTCTGCGGC AACAAGATCG TGGAGTCTGG CGAGGAATGC GACTGTGGCT   2820

TCAACGAGGA GGAGTGCAAG GACAAGTGCT GCTACCCGCG TCTGATCAGC GAGTACGACC   2880

AGTCGCTGAA CTCCAGTGCC AAGGGATGCA CGCGCCGCGC CAAGACCCAG TGCTCACCAT   2940

CGCAGGGTCC GTGCTGTCTG TCCAACTCCT GCACCTTTGT GCCGACGAGC TACCACCAGA   3000

AGTGCAAGGA GGAGACGGAG TGCAGCTGGT CGAGCACATG CAACGGAACC ACGGCCGAGT   3060

GTCCGGAGCC ACGTCATCGC GATGACAAGA CCATGTGCAA CAATGGAACA GCGCTATGCA   3120

TCCGCGGTGA ATGTAGTGGA TCGCCATGTT TGCTCTGGAA TATGACAAAG TGCTTCCTTA   3180

CCTCGACCAC ACTGCCGCAC GTGAGCAAGC GCAAGTTGTG CGACTTGGCC TGCCAGGATG   3240

GCAATGACAC CTCCACCTGC CGCAGCACCA GCGAGTTTGC CGATAAATAT AATATTCAAA   3300

AGGGTGGTAT TAGTCTGCAG CCCGGTTCGC CATGCGATAA TTTCCAGGGC TACTGCGATG   3360

TGTTCCTTAA GTGTCGAGCC GTGGATGCCG ATGGTCCGCT TCTTCGGCTG AAGAATTTGT   3420

TGCTCAACCG GAAGACCCTG CAAACGGTGG CCGAGTGGAT CGTCGACAAT TGGTACCTAG   3480

TGGTTCTGAT GGGAGTGGCC TTTATTGTGG TCATGGGTTC GTTCATCAAA TGTTGTGCCG   3540

TGCACACGCC CAGTTCCAAT CCGAAGAAGC GACGAGCTCG TCGAATCAGC GAAACTCTAA   3600

GAGCACCCAT GAACACGTTG CGTAGAATGC AACGTCATCC CAATCAGCGA GGAGCAGGTC   3660

CTCGAAGCAT CCCACCGCCG GCACATGAGG CGCAGCATTA TTCACGCGGC GGAGATGGTC   3720

GCGGCGGCGG CGGTGGAGGC GGAGGTCGCC ACGGTGGCTC TAGGTCACAC CATCAACAGC   3780

ATCCGCACGA TTGGGATCGT CATCAGGGTG GCCACTCAAT CGTCCCATTG CCCACCGGCG   3840

GCAGCCATTC AAGTCGCAAC TCGGCGGCGA ATCAAGCGAG AAGAAGCGAT GGACGAGGTC   3900

CACGATCCAC CAGCAGTGGG CGGCCGCAGG CTATAGCCAG CGGAAGCGGT GCCGCGAGCG   3960

GAGCAGCGCG ATCTCATGGC GGGTACGGAG CCGAACAGGC GATACCGGGT TCCATTGGTG   4020

GTGGTGTCCA GGCGGCCATT AGCAGCGGCG GTGTGGTGGC TCGGGCCCAG CTGCCGCTGC   4080

CATTGCCGCC GCCAAATGGA CAGCAGCAAA TGCAACAGCA ACAACAACTG CAACTACAGC   4140

AACCGGCAAT TTCGCCGCAG CAGCAGCCGC AGCAAGCGTT CTACACGCCG AAAGAACTAC   4200

CACCACGCAA TAAGTCCCGA TCATCACGTA CCAACAACAC CTCCAACACC ACAACCACCA   4260

CCAACTCATC CACAGCGGCA GCCGGCAGTG GGTCGGTCTC GGGACCGGGC TCGGGGCGG   4320

GCAGTAGTAG TAAGAGCAAG AGCGGTAAAA GTGCCAAAGC CAAAGACTCA AAGTCGCAAA   4380

AATCGCAGCA GGCCAACAAC AGTCGCAGCA GCAGCAAGGA GAAGGGCGTC AAGCCAGTGC   4440

GCCGAAATAT CGTTTATTAG GAGCGGAACC ATCACATTGC CATACACAAC ACTGAACGAA   4500

ATATAGCCCC GAACCCAAAA TATCAAATGC AACCACATAT AGAATCGCCC GCTGCTAGTC   4560

ATCGAACTAC ATGTATGAGT TGTTGCTTCC CATCCACCGA CAAACACAAA CAGAAAAGAA   4620

ATTATAATGA TATTTCATTT AATCGATGCA ATTGGCGTCG CGCCGCCTCC GCTACAAGTA   4680

AGCTTTAGTC GGCCGACATC GTTGCACGAG CAACAGCAGC AGCAACATCA TCTGCAGCAG   4740

CAGCAGCAGC ATCAGCAGCA ACTGGAGCCG CAGCAGCAAC ACGCCTATGC CGATGCTTAT   4800
```

```
GCGGCCTTGG GGCGGGGCCA GTATGAGTCC ACCACGCGGG CGCCCAACAA CAGCAAGGTT        4860

TGACAGCCAA AAGTAGCAAT GGAGCGCCAC AAAAGGCCAA AGGCTAAGCG ACTCAAGCAG        4920

CAGAAGGAGC CGCATACACA GCAAACAACA ACACAGCAAC AAAAGCAAAA ACAACATAAA        4980

TCAAATGAAC TCAAATTAAA TGTAAATGTA ATTTTTATGC TAATTATTTT TATTTAAACA        5040

GTGTTTGTAT GCCACAAGGG AAAACAGCCA GCAACAAAAA GAAAAATACA AAATAACAC         5100

AAAAAAGGAG ACAAATTTCG TAATACAGAA AAAGCTGAAA GTGAATGATA TTTTTGATTA        5160

ACTAAATTAA AATGAAAATA CGAATGCAAA TTATGAATAA TAAAAGTAAT TAAAAACGAC        5220

AACATGCATA ATACATATAA AGTTGCAAGT TGCATATATA TACATTTGTA TGTATATATT        5280

TATTATGGAT ACACAATTAT TAAATAGCAG CAGCCACAAC AAACAAGTAA TATACATGAA        5340

GAAAAACTAA GGTTTAATTG TATGAGAAAG CATTCTATAT GTCGGTGAGA TTTCTAAGCG        5400

CTAGGCCGAA ATACAAAATT AATTACACAC TTGAATAACA AAATGTGTTT TGTACAAAAA        5460

AAAAAAAATG AAATAAACAA AAACAGTGCG AATTAATTAA GCGTCATTAT AAAAAAAAGA        5520

ACGGAAACAA CAAAGCATTT AAATTGTATT TATCTGTACC GAAGCTAAAC GTTTATTTAA        5580

AGCCGTCAAA ATTGCATTTG TAAACTAGCA AAACAAAAAA AAAAAAAAC                    5630

(2) INFORMATION FOR SEQ ID NO: 2:

(i) SEQUENCE CHARACTERISTICS:
        (A) LENGTH: 1239 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Met Ser Ser Lys Cys Ala Phe Asn Ile Val Phe Val Ser Ile Ile Phe
1               5                   10                  15

Ile Ile Ile Val Asn Gly Tyr Ala Lys Asp Ile Ser Gly Val Lys Arg
            20                  25                  30

Gly His Glu Arg Leu Asn Glu Tyr Ile Ser His Tyr Glu Thr Leu Asn
        35                  40                  45

Tyr Asp His Glu His Ile Arg Ala Ser His Asn Arg Ala Arg Arg Ser
    50                  55                  60

Val Thr Lys Asp Gln Tyr Val His Leu Lys Phe Ala Ser His Gly Arg
65                  70                  75                  80

Asp Phe His Leu Arg Leu Lys Arg Asp Leu Asn Thr Phe Ser Asn Lys
                85                  90                  95

Leu Asp Phe Tyr Asp Ser Lys Gly Pro Ile Asp Val Ser Thr Asp His
            100                 105                 110

Ile Tyr Glu Gly Glu Val Ile Gly Asp Arg Asn Ser Tyr Val Phe Gly
        115                 120                 125

Ser Ile His Asn Gly Val Phe Glu Gly Lys Ile Ile Thr Glu Arg Asp
    130                 135                 140

Ala Tyr Tyr Val Glu His Ala Lys His Tyr Phe Pro Thr Asn Arg Thr
145                 150                 155                 160

Ala Thr Thr Thr Pro Pro Ser Thr Ser Thr Ser Ser Ala Thr Thr
                165                 170                 175

Val Thr Lys Ser Thr Gln Pro Thr Arg Pro Leu Ala Lys Ser Asn Thr
            180                 185                 190

Ser Thr Thr Ala Val Asn Ser Lys Thr Glu Asn Phe Ile Lys Lys Ile
        195                 200                 205
```

-continued

```
Ala Glu Ser Thr Thr Thr Ser Gln Gln Leu Pro Glu Tyr Thr Glu Ser
    210                 215                 220

Ser Ser Ser Ser Ser Thr Thr Thr Phe Pro Pro Thr Thr Glu Tyr Phe
225                 230                 235                 240

Glu Asp Glu Lys Glu Arg Asn Ala Glu Asp Glu Leu Asp Phe His Ser
            245                 250                 255

Ile Ile Tyr Lys Glu Ser His Val Glu Asp Ala Tyr Glu Asn Val Arg
            260                 265                 270

Glu Gly His Val Ala Gly Cys Gly Ile Thr Asp Glu Val Ser Gln Trp
        275                 280                 285

Met Glu Asn Ile Gln Asn Ser Ala Val Glu Glu Leu Pro Glu Pro Met
    290                 295                 300

Ser Lys Asp Tyr Gln Lys Leu His Arg Lys Gln Leu His Lys Lys Ser
305                 310                 315                 320

Ala Pro Gln Gln Gln Gln Pro His Pro Pro Lys Lys Tyr Ile Ser
            325                 330                 335

Gly Asp Glu Asp Phe Lys Tyr Pro His Gln Lys Tyr Thr Lys Glu Ala
            340                 345                 350

Asn Phe Ala Glu Gly Ala Phe Tyr Asp Pro Ser Thr Gly Arg Arg Leu
            355                 360                 365

Gly Ser Ser Ala Asn Val Ala Asp Trp His Gln Leu Val His Glu Arg
        370                 375                 380

Val Arg Arg Ala Thr Asp Asn Gly Ala Gly Asp Arg Gly Ser Ser Gly
385                 390                 395                 400

Gly Ser Gly Arg Gly Arg Glu Asp Asn Lys Asn Thr Cys Ser Leu Tyr
            405                 410                 415

Ile Gln Thr Asp Pro Leu Ile Trp Arg His Ile Arg Glu Gly Ile Ala
            420                 425                 430

Asp His Asp Arg Gly Arg Lys Tyr Glu Val Asp Glu Lys Thr Arg Glu
        435                 440                 445

Glu Ile Thr Ser Leu Ile Ala His His Val Thr Ala Val Asn Tyr Ile
    450                 455                 460

Tyr Arg Asn Thr Lys Phe Asp Gly Arg Thr Glu His Arg Asn Ile Arg
465                 470                 475                 480

Phe Glu Val Gln Arg Ile Lys Ile Asp Asp Asp Ser Ala Cys Arg Asn
            485                 490                 495

Ser Tyr Asn Gly Pro His Asn Ala Phe Cys Asn Glu His Met Asp Val
            500                 505                 510

Ser Asn Phe Leu Asn Leu His Ser Leu Glu Asp His Ser Asp Phe Cys
        515                 520                 525

Leu Ala Tyr Val Phe Thr Tyr Arg Asp Phe Thr Gly Thr Leu Gly
    530                 535                 540

Leu Ala Trp Val Ala Ser Ala Ser Gly Ala Ser Gly Gly Ile Cys Glu
545                 550                 555                 560

Lys Tyr Lys Thr Tyr Thr Glu Thr Val Gly Gly Gln Tyr Gln Ser Thr
            565                 570                 575

Lys Arg Ser Leu Asn Thr Gly Ile Ile Thr Phe Val Asn Tyr Asn Ser
            580                 585                 590

Arg Val Pro Pro Lys Val Ser Gln Leu Thr Leu Ala His Glu Ile Gly
        595                 600                 605

His Asn Phe Gly Ser Pro His Asp Tyr Pro Gln Glu Cys Arg Pro Gly
    610                 615                 620
```

-continued

```
Gly Leu Asn Gly Asn Tyr Ile Met Phe Ala Ser Ala Thr Ser Gly Asp
625                 630                 635                 640

Arg Pro Asn Asn Ser Lys Phe Ser Pro Cys Ser Ile Arg Asn Ile Ser
                645                 650                 655

Asn Val Leu Asp Val Leu Val Gly Asn Thr Lys Arg Asp Cys Phe Lys
                660                 665                 670

Ala Ser Glu Gly Ala Phe Cys Gly Asn Lys Ile Val Glu Ser Gly Glu
                675                 680                 685

Glu Cys Asp Cys Gly Phe Asn Glu Glu Cys Lys Asp Lys Cys Cys
690                 695                 700

Tyr Pro Arg Leu Ile Ser Glu Tyr Asp Gln Ser Leu Asn Ser Ser Ala
705                 710                 715                 720

Lys Gly Cys Thr Arg Ala Lys Thr Gln Cys Ser Pro Ser Gln Gly
                725                 730                 735

Pro Cys Cys Leu Ser Asn Ser Cys Thr Phe Val Pro Thr Ser Tyr His
                740                 745                 750

Gln Lys Cys Lys Glu Thr Glu Cys Ser Trp Ser Ser Thr Cys Asn
                755                 760                 765

Gly Thr Thr Ala Glu Cys Pro Glu Pro Arg His Arg Asp Asp Lys Thr
770                 775                 780

Met Cys Asn Asn Gly Thr Ala Leu Cys Ile Arg Gly Glu Cys Ser Gly
785                 790                 795                 800

Ser Pro Cys Leu Leu Trp Asn Met Thr Lys Cys Phe Leu Thr Ser Thr
                805                 810                 815

Thr Leu Pro His Val Ser Lys Arg Lys Leu Cys Asp Leu Ala Cys Gln
                820                 825                 830

Asp Gly Asn Asp Thr Ser Thr Cys Arg Ser Thr Ser Glu Phe Ala Asp
                835                 840                 845

Lys Tyr Asn Ile Gln Lys Gly Gly Ile Ser Leu Gln Pro Gly Ser Pro
850                 855                 860

Cys Asp Asn Phe Gln Gly Tyr Cys Asp Val Phe Leu Lys Cys Arg Ala
865                 870                 875                 880

Val Asp Ala Asp Gly Pro Leu Leu Arg Leu Lys Asn Leu Leu Leu Asn
                885                 890                 895

Arg Lys Thr Leu Gln Thr Val Ala Glu Trp Ile Val Asp Asn Trp Tyr
                900                 905                 910

Leu Val Val Leu Met Gly Val Ala Phe Ile Val Val Met Gly Ser Phe
                915                 920                 925

Ile Lys Cys Cys Ala Val His Thr Pro Ser Ser Asn Pro Lys Lys Arg
930                 935                 940

Arg Ala Arg Arg Ile Ser Glu Thr Leu Arg Ala Pro Met Asn Thr Leu
945                 950                 955                 960

Arg Arg Met Gln Arg His Pro Asn Gln Arg Gly Ala Gly Pro Arg Ser
                965                 970                 975

Ile Pro Pro Pro Ala His Glu Ala Gln His Tyr Ser Arg Gly Gly Asp
                980                 985                 990

Gly Arg Gly Gly Gly Gly Gly Gly Arg His Gly Gly Ser Arg
                995                 1000                1005

Ser His His Gln Gln His Pro His Asp Trp Asp Arg His Gln Gly Gly
        1010                1015                1020

His Ser Ile Val Pro Leu Pro Thr Gly Gly Ser His Ser Ser Arg Asn
1025                1030                1035                1040

Ser Ala Ala Asn Gln Ala Arg Arg Ser Asp Gly Arg Gly Pro Arg Ser
```

-continued

```
              1045           1050            1055
Thr Ser Ser Gly Arg Pro Gln Ala Ile Ala Ser Gly Ser Gly Ala Ala
                    1060            1065            1070

Ser Gly Ala Ala Arg Ser His Gly Gly Tyr Gly Ala Glu Gln Ala Ile
        1075            1080            1085

Pro Gly Ser Ile Gly Gly Val Gln Ala Ala Ile Ser Ser Gly Gly
    1090            1095            1100

Val Val Ala Arg Ala Gln Leu Pro Leu Pro Leu Pro Pro Asn Gly
1105            1110            1115            1120

Gln Gln Gln Met Gln Gln Gln Gln Leu Gln Leu Gln Pro Ala
                1125            1130            1135

Ile Ser Pro Gln Gln Gln Pro Gln Gln Ala Phe Tyr Thr Pro Lys Glu
        1140            1145            1150

Leu Pro Pro Arg Asn Lys Ser Arg Ser Ser Arg Thr Asn Asn Thr Ser
        1155            1160            1165

Asn Thr Thr Thr Thr Thr Asn Ser Ser Thr Ala Ala Ala Gly Ser Gly
    1170            1175            1180

Ser Val Ser Gly Pro Gly Ser Gly Ala Gly Ser Ser Ser Lys Ser Lys
1185            1190            1195            1200

Ser Gly Lys Ser Ala Lys Ala Lys Asp Ser Lys Ser Gln Lys Ser Gln
                1205            1210            1215

Gln Ala Asn Asn Ser Arg Ser Ser Ser Lys Glu Lys Gly Val Lys Pro
        1220            1225            1230

Val Arg Arg Asn Ile Val Tyr
        1235
```

(2) INFORMATION FOR SEQ ID NO: 3:

(i) SEQUENCE CHARACTERISTICS:
        (A) LENGTH: 2796 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

```
GAATTCCGGG TTTTGGAGGA GCTAGGAGCG TTGCCGGCCC CTGAAGTGGA GCGAGAGGGA      60

GGTGCTTTCG CCGTTCTCCT GCCAGGGGAG GTCCCGGCTT CCCGTGGAGG CTCCGGACCA     120

AGCCCCTTCA GCTTCTCCCT CCGGATCGAT GTGCTGCTGT TAACCCGTGA GGAGGCGGCG     180

GCGGCGGCAG CGGCAGCGGA AGATGGTGTT GCTGAGAGTG TTAATTCTGC TCCTCTCCTG     240

GGCGGCGGGG ATGGGAGGTC AGTATGGGAA TCCTTTAAAT AAATATATCA GACATTATGA     300

AGGATTATCT TACAATGTGG ATTCATTACA CCAAAAACAC CAGCGTGCCA AAAGAGCAGT     360

CTCACATGAA GACCAATTTT TACGTCTAGA TTTCCATGCC CATGGAAGAC ATTTCAACCT     420

ACGAATGAAG AGGGACACTT CCCTTTTCAG TGATGAATTT AAAGTAGAAA CATCAAATAA     480

AGTACTTGAT TATGATACCT CTCATATTTA CACTGGACAT ATTTATGGTG AAGAAGGAAG     540

TTTAGCCATG GGTCTGTTAT TGATGGAAGA TTTGAAGGAT TCATCCAGAC TCGTGGTGGC     600

ACATTTTATG TTTGAGCCAG CAGAGAGATA TATTAAAGAC CGAACTCTGC CATTTCACTC     660

TGTCATTTAT CATGAAGATG ATATTAACTA TCCCCATAAA TACGGTCCTC AGGGGGGCTG     720

TGCAGATCAT TCAGTATTTG AAAGAATGAG GAAATACCAG ATGACTGGTG TAGAGGAAGT     780

AACACAGATA CCTCAAGAAG AACATGCTGC TAATGGTCCA GAACTTCTGA GGAAAAAACG     840
```

-continued

| | | | | |
|---|---|---|---|---|
|TACAAATTCA|GCTGAAAAAA|ATACTTGTCA|GCTTTATATT|CAGACTGATC ATTTGTTCTT 900|
|TAAATATTAC|GGAACACGAG|AAGCTGTGAT|TGCCCAGATA|TCCAGTCATG TTAAAGCGAT 960|
|TGATACAATT|TACCAGACCA|CAGACTTCTC|CGGAATCCGT|AACATCAGTT TCATGGTGAA 1020|
|ACGCATAAGA|ATCAATACAA|CTGCTGATGA|GAAGGACCCT|ACAAATCCTT TCCGTTTCCC 1080|
|AAATATTGGT|GTGGAGAAGT|TTCTGGAATT|GAATTCTGAG|CAGAATCATG ATGACTACTG 1140|
|TTTGGCCTAT|GTCTTCACAG|ACCGAGATTT|TGATGATGGC|GTACTTGGTC TGGCTTGGGT 1200|
|TGGAGCACCT|TCAGGAAGCT|CTGGAGGAAT|ATGTGAAAAA|AGTAAACTCT ATTCAGATGG 1260|
|TAAGAAGAAG|TCCTTAAACA|CTGGAATTAT|TACTGTTCAG|AACTATGGGT CTCATGTACC 1320|
|TCCCAAAGTC|TCTCACATTA|CTTTTGCTCA|CGAAGTTGGA|CATAACTTTG GATCCCCACA 1380|
|TGATTCTGGA|ACAGAGTGCA|CACCAGGAGA|ATCTAAGAAT|TTGGGTCAAA AGAAAATGG 1440|
|CAATTACATC|ATGTATGCAA|GAGCAACATC|TGGGACAAA|CTTAACAACA ATAAATTCTC 1500|
|ACTCTGTAGT|ATTAGAAATA|TAAGCCAAGT|TCTTGAGAAG|AAGAGAAACA ACTGTTTTGT 1560|
|TGAATCTGGC|CAACCTATTT|GTGGAAATGG|AATGGTAGAA|CAAGGTGAAG AATGTGATTG 1620|
|TGGCTATAGT|GACCAGTGTA|AAGATGAATG|CTGCTTCGAT|GCAAATCAAC CAGAGGGAAG 1680|
|AAAATGCAAA|CTGAAACCTG|GAAACAGTG|CAGTCCAAGT|CAAGGTCCTT GTTGTACAGC 1740|
|ACAGTGTGCA|TTCAAGTCAA|AGTCTGAGAA|GTGTCGGGAT|GATTCAGACT GTGCAAGGGA 1800|
|AGGAATATGT|AATGGCTTCA|CAGCTCTCTG|CCCAGCATCT|GACCCTAAAC CAAACTTCAC 1860|
|AGACTGTAAT|AGGCATACAC|AAGTGTGCAT|TAATGGGCAA|TGTGCAGGTT CTATCTGTGA 1920|
|GAAATATGGC|TTAGAGGAGT|GTACGTGTGC|CAGTTCTGAT|GGCAAAGATG ATAAAGAATT 1980|
|ATGCCATGTA|TGCTGTATGA|AGAAAATGGA|CCCATCAACT|TGTGCCAGTA CAGGGTCTGT 2040|
|GCAGTGGAGT|AGGCACTTCA|GTGGTCGAAC|CATCACCCTG|CAACCTGGAT CCCCTTGCAA 2100|
|CGATTTTAGA|GGTTACTGTG|ATGTTTTCAT|GCGGTGCAGA|TTAGTAGATG CTGATGGTCC 2160|
|TCTAGCTAGG|CTTAAAAAAG|CAATTTTTAG|TCCAGAGCTC|TATGAAAACA TTGCTGAATG 2220|
|GATTGTGGCT|CATTGGTGGG|CAGTATTACT|TATGGGAATT|GCTCTGATCA TGCTAATGGC 2280|
|TGGATTTATT|AAGATATGCA|GTGTTCATAC|TCCAAGTAGT|AATCCAAAGT TGCCTCCTCC 2340|
|TAAACCACTT|CCAGGCACTT|TAAAGAGGAG|GAGACCTCCA|CAGCCCATTC AGCAACCCCA 2400|
|GCGTCAGCGG|CCCCGAGAGA|GTTATCAAAT|GGGACACATG|AGACGCTAAC TGCAGCTTTT 2460|
|GCCTTGGTTC|TTCCTAGTGC|CTACAATGGG|AAAACTTCAC|TCCAAAGAGA AACCTATTAA 2520|
|GTCATCATCT|CCAAACTAAA|CCCTCACAAG|TAACAGTTGA|AGAAAAAATG GCAAGAGATC 2580|
|ATATCCTCAG|ACCAGGTGGA|ATTACTTAAA|TTTTAAAGCC|TGAAAATTCC AATTTGGGGG 2640|
|TGGGAGGTGG|AAAAGGAACC|CAATTTTCTT|ATGAACAGAT|ATTTTTAACT TAATGGCACA 2700|
|AAGTCTTAGA|ATATTATTAT|GTGCCCCGTG|TTCCCTGTTC|TTCGTTGCTG CATTTTCTTC 2760|
|ACTTGCAGGC|AAACTTGGCT|CTCAATAAAC|TTTTCG| 2796|

(2) INFORMATION FOR SEQ ID NO: 4:

(i) SEQUENCE CHARACTERISTICS:
        (A) LENGTH: 748 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

-continued

```
Met Val Leu Leu Arg Val Leu Ile Leu Leu Ser Trp Ala Ala Gly
1               5                   10                  15

Met Gly Gly Gln Tyr Gly Asn Pro Leu Asn Lys Tyr Ile Arg His Tyr
            20                  25                  30

Glu Gly Leu Ser Tyr Asn Val Asp Ser Leu His Gln Lys His Gln Arg
            35                  40                  45

Ala Lys Arg Ala Val Ser His Glu Asp Gln Phe Leu Arg Leu Asp Phe
50                  55                  60

His Ala His Gly Arg His Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
                100                 105                 110

Ser Leu Ala Met Gly Leu Leu Leu Met Glu Asp Leu Lys Asp Ser Ser
            115                 120                 125

Arg Leu Val Val Ala His Phe Met Phe Glu Pro Ala Glu Arg Tyr Ile
130                 135                 140

Lys Asp Arg Thr Leu Pro Phe His Ser Val Ile Tyr His Glu Asp Asp
145                 150                 155                 160

Ile Asn Tyr Pro His Lys Tyr Gly Pro Gln Gly Gly Cys Ala Asp His
                165                 170                 175

Ser Val Phe Glu Arg Met Arg Lys Tyr Gln Met Thr Gly Val Glu Glu
            180                 185                 190

Val Thr Gln Ile Pro Gln Glu Glu His Ala Ala Asn Gly Pro Glu Leu
            195                 200                 205

Leu Arg Lys Lys Arg Thr Asn Ser Ala Glu Lys Asn Thr Cys Gln Leu
210                 215                 220

Tyr Ile Gln Thr Asp His Leu Phe Phe Lys Tyr Tyr Gly Thr Arg Glu
225                 230                 235                 240

Ala Val Ile Ala Gln Ile Ser Ser His Val Lys Ala Ile Asp Thr Ile
                245                 250                 255

Tyr Gln Thr Thr Asp Phe Ser Gly Ile Arg Asn Ile Ser Phe Met Val
            260                 265                 270

Lys Arg Ile Arg Ile Asn Thr Thr Ala Asp Glu Lys Asp Pro Thr Asn
            275                 280                 285

Pro Phe Arg Phe Pro Asn Ile Gly Val Glu Lys Phe Leu Glu Leu Asn
290                 295                 300

Ser Glu Gln Asn His Asp Asp Tyr Cys Leu Ala Tyr Val Phe Thr Asp
305                 310                 315                 320

Arg Asp Phe Asp Asp Gly Val Leu Gly Leu Ala Trp Val Gly Ala Pro
                325                 330                 335

Ser Gly Ser Ser Gly Gly Ile Cys Glu Lys Ser Lys Leu Tyr Ser Asp
            340                 345                 350

Gly Lys Lys Lys Ser Leu Asn Thr Gly Ile Ile Thr Val Gln Asn Tyr
            355                 360                 365

Gly Ser His Val Pro Pro Lys Val Ser His Ile Thr Phe Ala His Glu
370                 375                 380

Val Gly His Asn Phe Gly Ser Pro His Asp Ser Gly Thr Glu Cys Thr
385                 390                 395                 400

Pro Gly Glu Ser Lys Asn Leu Gly Gln Lys Glu Asn Gly Asn Tyr Ile
                405                 410                 415

Met Tyr Ala Arg Ala Thr Ser Gly Asp Lys Leu Asn Asn Asn Lys Phe
```

```
                    420                 425                 430
Ser Leu Cys Ser Ile Arg Asn Ile Ser Gln Val Leu Glu Lys Lys Arg
        435                 440                 445

Asn Asn Cys Phe Val Glu Ser Gly Gln Pro Ile Cys Gly Asn Gly Met
    450                 455                 460

Val Glu Gln Gly Glu Glu Cys Asp Cys Gly Tyr Ser Asp Gln Cys Lys
465                 470                 475                 480

Asp Glu Cys Cys Phe Asp Ala Asn Gln Pro Glu Gly Arg Lys Cys Lys
                485                 490                 495

Leu Lys Pro Gly Lys Gln Cys Ser Pro Ser Gln Gly Pro Cys Cys Thr
            500                 505                 510

Ala Gln Cys Ala Phe Lys Ser Lys Ser Glu Lys Cys Arg Asp Asp Ser
        515                 520                 525

Asp Cys Ala Arg Glu Gly Ile Cys Asn Gly Phe Thr Ala Leu Cys Pro
    530                 535                 540

Ala Ser Asp Pro Lys Pro Asn Phe Thr Asp Cys Asn Arg His Thr Gln
545                 550                 555                 560

Val Cys Ile Asn Gly Gln Cys Ala Gly Ser Ile Cys Glu Lys Tyr Gly
                565                 570                 575

Leu Glu Glu Cys Thr Cys Ala Ser Ser Asp Gly Lys Asp Asp Lys Glu
            580                 585                 590

Leu Cys His Val Cys Cys Met Lys Lys Met Asp Pro Ser Thr Cys Ala
        595                 600                 605

Ser Thr Gly Ser Val Gln Trp Ser Arg His Phe Ser Gly Arg Thr Ile
    610                 615                 620

Thr Leu Gln Pro Gly Ser Pro Cys Asn Asp Phe Arg Gly Tyr Cys Asp
625                 630                 635                 640

Val Phe Met Arg Cys Arg Leu Val Asp Ala Asp Gly Pro Leu Ala Arg
                645                 650                 655

Leu Lys Lys Ala Ile Phe Ser Pro Glu Leu Tyr Glu Asn Ile Ala Glu
            660                 665                 670

Trp Ile Val Ala His Trp Trp Ala Val Leu Leu Met Gly Ile Ala Leu
        675                 680                 685

Ile Met Leu Met Ala Gly Phe Ile Lys Ile Cys Ser Val His Thr Pro
    690                 695                 700

Ser Ser Asn Pro Lys Leu Pro Pro Lys Pro Leu Pro Gly Thr Leu
705                 710                 715                 720

Lys Arg Arg Arg Pro Pro Gln Pro Ile Gln Gln Pro Gln Arg Gln Arg
                725                 730                 735

Pro Arg Glu Ser Tyr Gln Met Gly His Met Arg Arg
            740                 745
```

(2) INFORMATION FOR SEQ ID NO: 5:

(i) SEQUENCE CHARACTERISTICS:
        (A) LENGTH: 2098 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

```
GAATTCTGAG CAGAATCATG ATGACTACTG TTTGGCCTAT GTCTTCACAG ACCGAGATTT     60

TGATGATGGC GTACTTGGTC TGGCTTGGGT TGGAGCACCT TCAGGAAGCT CTGGAGGAAT    120
```

```
ATGTGAAAAA AGTAAACTCT ATTCAGATGG TAAGAAGAAG TCCTTAAACA CTGGAATTAT       180

TACTGTTCAG AACTATGGGT CTCATGTACC TCCCAAAGTC TCTCACATTA CTTTTGCTCA       240

CGAAGTTGGA CATAACTTTG GATCCCCACA TGATTCTGGA ACAGAGTGCA CACCAGGAGA       300

ATCTAAGAAT TTGGGTCAAA AGAAAATGG CAATTACATC ATGTATGCAA GAGCAACATC       360

TGGGACAAA CTTAACAACA ATAAATTCTC ACTCTGTAGT ATTAGAAATA TAAGCCAAGT       420

TCTTGAGAAG AAGAGAAACA ACTGTTTTGT TGAATCTGGC CAACCTATTT GTGGAAATGG       480

AATGGTAGAA CAAGGTGAAG AATGTGATTG TGGCTATAGT GACCAGTGTA AAGATGAATG       540

CTGCTTCGAT GCAAATCAAC CAGAGGGAAG AAAATGCAAA CTGAAACCTG GAAACAGTG       600

CAGTCCAAGT CAAGGTCCTT GTTGTACAGC ACAGTGTGCA TTCAAGTCAA AGTCTGAGAA       660

GTGTCGGGAT GATTCAGACT GTGCAAGGGA AGGAATATGT AATGGCTTCA CAGCTCTCTG       720

CCCAGCATCT GACCCTAAAC CAAACTTCAC AGACTGTAAT AGGCATACAC AAGTGTGCAT       780

TAATGGGGTA AGCATTTAAC TATATGTTTT AAAATTTAAT TTTAGAAAAC TTGTTTTTCA       840

GAAGAATTAT TGATGCTTAA AGCTACATAG TTAAAGTAAT TAATCTTGGT CTCTGTTTAA       900

GTAATATTCC CTCACAAAAC CATGAATATA TTATGTGGCA TTCAATTAGC TACTAATTTG       960

TCTTTCATCT TTCCATGTAC ATGTGGTTGA TATTCTCTAG AGAAACATAG TTGTACAACT      1020

CGGCATGTGA TTTGTCTATA ATATTTAAGT TTTATAAAAT AATATTTCAG TAGCCTAAAT      1080

AAAAGAACTC TTTGGTCATC TTCTCTGAAT ATCAAACCTT CAAAGCTTTT GTGGCTGAAT      1140

ATCACTTTGC TCTACAGGAA AAAAATTTAA TTTTTCTTTC TTTATAGAAG AGCCGTAATA      1200

ACCAACATAA AATCGATCCT CATCTAATCT CTTGCTCTGC TTTTATTTCA TTTTTTTAAG      1260

TTGCCATTGC TTTAAAAGAT TTACTATCTT TCTTGGATTT ACTGTTTTC AAATTTTTTC      1320

AAATGTATTT ATGTAATTCA GTTTTGATAC TCATCTCTGT TTGTTTTTCA CTTTCATTTC      1380

CATTTAAATA TTTTGACATT GGAAGCTCAT ACTTGCCTGT CTGTTACTAT AAAAAATAGG      1440

TTTGACTGTA TAGGGATTAA ACAATTTGTC TTTTATTTTC TTCTAGCAAT GTGCAGGTTC      1500

TATCTGTGAG AAATATGGCT TAGAAGAGTG TACGTGTGCC AGTCTGATGG CAAAGATGAT      1560

AAAGAATTAT GCCATGTATG CTGTATGAAG AAAAGTAAGG CTTTTAAAAA CACAAGATAT      1620

AAAATTTGCC TCAAACTATT ATTTTCTCCT AAATTTAAG TGTAAAACTT TGACCTACAG      1680

TTTGGCCAGA TAATTTCCAG CTAAATCTGT CCTCTTGAGG AGATTATAAA TGTAACGTAG      1740

CATTGTGTCT CTATTATTAT GGTCTCTACA ATGTTTTAAA AATGATAAAC TAGACAAAAC      1800

GTTGCCAGCT TTACAGCAGT AATTTACATA AACACTGTTA GACTTTAAGT CATCGTGGAC      1860

ACTGAGTCAA GACTTGCTGG TTGCTTGTTT ACATTGTAAC ATTTAATATG AATTACTGAT      1920

GGCGTTACCC AGCCTAACTA GAGAAGGTCT GTATAACATG TTATGGTAAT GATTTCAGTT      1980

TTTTTTCCCT CTTTGTATTT GCACAACTGG GAAATCTGAT CTGCAACTTA TATTTGAATC      2040

TGACCTTCAG CTTATATTTG GCATTTCTTT TCCAGTGGAC CCATCAACTC CGGAATTC       2098
```

(2) INFORMATION FOR SEQ ID NO: 6:

(i) SEQUENCE CHARACTERISTICS:
        (A) LENGTH: 265 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Asn Ser Glu Gln Asn His Asp Asp Tyr Cys Leu Ala Tyr Val Phe Thr
 1               5                  10                 15

Asp Arg Asp Phe Asp Asp Gly Val Leu Gly Leu Ala Trp Val Gly Ala
                20                  25                 30

Pro Ser Gly Ser Ser Gly Gly Ile Cys Glu Lys Ser Lys Leu Tyr Ser
            35                  40                 45

Asp Gly Lys Lys Lys Ser Leu Asn Thr Gly Ile Ile Thr Val Gln Asn
        50                  55                 60

Tyr Gly Ser His Val Pro Pro Lys Val Ser His Ile Thr Phe Ala His
65                  70                  75                 80

Glu Val Gly His Asn Phe Gly Ser Pro His Asp Ser Gly Thr Glu Cys
                85                  90                 95

Thr Pro Gly Glu Ser Lys Asn Leu Gly Gln Lys Glu Asn Gly Asn Tyr
            100                 105                110

Ile Met Tyr Ala Arg Ala Thr Ser Gly Asp Lys Leu Asn Asn Asn Lys
        115                 120                125

Phe Ser Leu Cys Ser Ile Arg Asn Ile Ser Gln Val Leu Glu Lys Lys
    130                 135                 140

Arg Asn Asn Cys Phe Val Glu Ser Gly Gln Pro Ile Cys Gly Asn Gly
145                 150                 155                160

Met Val Glu Gln Gly Glu Glu Cys Asp Cys Gly Tyr Ser Asp Gln Cys
                165                 170                175

Lys Asp Glu Cys Cys Phe Asp Ala Asn Gln Pro Glu Gly Arg Lys Cys
            180                 185                190

Lys Leu Lys Pro Gly Lys Gln Cys Ser Pro Ser Gln Gly Pro Cys Cys
        195                 200                 205

Thr Ala Gln Cys Ala Phe Lys Ser Lys Ser Glu Lys Cys Arg Asp Asp
    210                 215                 220

Ser Asp Cys Ala Arg Glu Gly Ile Cys Asn Gly Phe Thr Ala Leu Cys
225                 230                 235                240

Pro Ala Ser Asp Pro Lys Pro Asn Phe Thr Asp Cys Asn Arg His Thr
                245                 250                255

Gln Val Cys Ile Asn Gly Val Ser Ile
            260                 265

(2) INFORMATION FOR SEQ ID NO: 7:

(i) SEQUENCE CHARACTERISTICS:
        (A) LENGTH: 2481 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

CCGTGAGGAG GCGGCGGCCG GGAAGATGGT GTTGCCGACA GTGTTAATTC TGCTCCTCTC      60

CTGGGCGGCG GGCTGGGAG GTCAGTATGG AAATCCTTTA AATAAATATA TTAGACATTA     120

TGAAGGATTA TCTTACAATG TGGATTCATT ACACCAAAAA CACCAGCGTG CCAAACGAGC    180

AGTCTCACAT GAGGACCAGT TTTTACTTCT AGATTTCCAT GCTCATGGAA GACAGTTCAA    240

CCTACGAATG AAGAGGGACA CTTCCCTTTT TAGTGATGAA TTTAAAGTAG AAACATCAAA    300

TAAAGTACTT GATTATGATA CCTCTCATAT TTACACTGGA CATATTTATG GTGAAGAAGG    360

AAGCTTTAGT CATGGGTCTG TCATTGATGG AAGATTTGAA GGTTTCATCA AGACTCGTGG    420

TGGCACGTTT TACATTGAGC CAGCAGAGAG ATACATTAAA GATCGAATCC TGCCATTTCA    480
```

```
CTCTGTCATT TATCATGAAG ATGATATTAA CTATCCCCAT AAATACGGCC CACAGGGGGG      540

CTGTGCAGAT CACTCCGTTT TTGAAAGGAT GAGGAAGTAC CAAATGACTG GAGTAGAGGA      600

AGGAGCCCGG GCACATCCAG AGAAGCATGC TGCTAGTAGT GGTCCTGAGC TCCTGAGGAA      660

AAAACGCACA ACTCTGGCTG AAAGAAATAC TTGTCAGCTC TATATCCAGA CAGATCACCT      720

GTTCTTTAAA TACTATGGAA CACGAGAAGC TGTGATTGCT CAGATATCCA GTCATGTTAA      780

AGCAATTGAT ACAATTTACC AGACTACAGA CTTCTCCGGA ATCCGTAACA TCAGCTTCAT      840

GGTGAAACGC ATAAGAATCA ATACAACCTC TGATGAAAAA GACCCTACAA ATCCTTTCCG      900

TTTCCCAAAT ATTGGTGTGG AGAAGTTCCT GGAGTTGAAT TCTGAGCAGA ATCATGATGA      960

CTACTGCCTG GCCTATGTCT TCACAGACCG GGATTTTGAT GATGGTGTTC TTGGTCTGGC     1020

CTGGGTTGGA GCACCTTCAG GAAGCTCTGG GGGAATATGT GAGAAAGCA AGTTGTATTC     1080

AGATGGCAAG AAGAAGTCAT TGAACACAGG CATCATTACT GTTCAGAACT ATGGCTCCCA     1140

TGTGCCTCCC AAAGTCTCTC ATATTACGTT TGCTCATGAA GTTGGACATA ACTTTGGATC     1200

TCCACATGAT TCTGGAACAG AGTGTACTCC AGGAGAGTCT AAGAACTTAG GACAAAAAGA     1260

AAATGGCAAT TACATCATGT ATGCAAGAGC AACATCTGGG GACAAACTTA CAACAACAA     1320

ATTTTCACTC TGCAGCATTA GAAACATAAG CCAAGTGCTT GAGAAGAAGA GGAACAACTG     1380

TTTTGTTGAA TCTGGCCAGC CTATCTGTGG AAACGGGATG GTGGAACAAG GGGAAGAGTG     1440

TGACTGTGGC TACAGTGACC AGTGCAAAGA TGATTGCTGC TTCGATGCCA ACCAGCCAGA     1500

GGGGAAGAAA TGCAAGCTGA AGCCTGGGAA GCAGTGCAGT CCGAGTCAAG GACCCTGCTG     1560

TACAGCACAG TGTGCATTCA AGTCAAAGTC TGAAAAGTGC CGGGATGATT CTGACTGTGC     1620

AAAGGAAGGG ATATGCAATG GCTTCACAGC CCTTTGCCCA GCATCTGATC CCAAGCCCAA     1680

CTTTACAGAC TGTAACAGGC ACACACAAGT GTGCATTAAT GGGCAATGTG CAGGTTCTAT     1740

TTGTGAAAAG TATGACTTGG AGGAGTGCAC CTGTGCCAGC TCTGATGGCA AGATAATAA     1800

GGAATTATGC CATGTTTGCT GCATGAAGAA AATGGCTCCA TCAACTTGTG CCAGTACAGG     1860

CTCTTTGCAG TGGAGCAAGC AGTTCAGTGG TCGGACTATC ACTCTGCAGC CGGGCTCTCC     1920

ATGTAATGAC TTCAGAGGCT ACTGTGATGT TTTCATGCGG TGCAGATTAG TAGATGCTGA     1980

TGGCCCTCTA GCTAGGCTGA AAAAAGCCAT TTTTAGTCCA CAACTCTATG AAAACATTGC     2040

TGAGTGGATT GTGGCTCACT GGTGGGCAGT ACTGCTTATG GGAATTGCCC TGATCATGTT     2100

AATGGCTGGA TTTATCAAGA TTTGCAGTGT TCACACTCCA AGTAGTAATC AAAGTTGCC     2160

GCCTCCTAAA CCACTTCCAG GCACTTTAAA GAGGAGGAGA CCGCCACAGC CCATTCAGCA     2220

GCCCCCGCGT CAGAGGCCCC GAGAGAGTTA TCAAATGGGA CACATGCGAC GCTAATGCAG     2280

CTTTTGCCTT GGTTCTTCCT AGTGCCTACA GTGGGAAAAC TTCACTCCAA AGAGAAACCT     2340

GTTAAGTCAT CATCTGCAAA TGATACCCTT ACAGTTAATA GTTGAAGAAA AAATGGCAAG     2400

AGATCATGTC CTCAGATCAG GTGGAATTAC TCAAAATTTA AAGCCTGAAA ATTCCAATTT     2460

TGGGGGTGGG GGTGGGATGG G                                              2481
```

(2) INFORMATION FOR SEQ ID NO: 8:

(i) SEQUENCE CHARACTERISTICS:
        (A) LENGTH: 749 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Met Val Leu Pro Thr Val Leu Ile Leu Leu Ser Trp Ala Ala Gly
1               5                   10                  15

Leu Gly Gly Gln Tyr Gly Asn Pro Leu Asn Lys Tyr Ile Arg His Tyr
            20                  25                  30

Glu Gly Leu Ser Tyr Asn Val Asp Ser Leu His Gln Lys His Gln Arg
        35                  40                  45

Ala Lys Arg Ala Val Ser His Glu Asp Gln Phe Leu Leu Leu Asp Phe
    50                  55                  60

His Ala His Gly Arg Gln Phe Asn Leu Arg Met Lys Arg Asp Thr Ser
65                  70                  75                  80

Leu Phe Ser Asp Glu Phe Lys Val Glu Thr Ser Asn Lys Val Leu Asp
                85                  90                  95

Tyr Asp Thr Ser His Ile Tyr Thr Gly His Ile Tyr Gly Glu Glu Gly
            100                 105                 110

Ser Phe Ser His Gly Ser Val Ile Asp Gly Arg Phe Glu Gly Phe Ile
        115                 120                 125

Lys Thr Arg Gly Gly Thr Phe Tyr Ile Glu Pro Ala Glu Arg Tyr Ile
    130                 135                 140

Lys Asp Arg Ile Leu Pro Phe His Ser Val Ile Tyr His Glu Asp Asp
145                 150                 155                 160

Ile Asn Tyr Pro His Lys Tyr Gly Pro Gln Gly Gly Cys Ala Asp His
                165                 170                 175

Ser Val Phe Glu Arg Met Arg Lys Tyr Gln Met Thr Gly Val Glu Glu
            180                 185                 190

Gly Ala Arg Ala His Pro Glu Lys His Ala Ala Ser Ser Gly Pro Glu
        195                 200                 205

Leu Leu Arg Lys Lys Arg Thr Thr Leu Ala Glu Arg Asn Thr Cys Gln
    210                 215                 220

Leu Tyr Ile Gln Thr Asp His Leu Phe Phe Lys Tyr Tyr Gly Thr Arg
225                 230                 235                 240

Glu Ala Val Ile Ala Gln Ile Ser Ser His Val Lys Ala Ile Asp Thr
                245                 250                 255

Ile Tyr Gln Thr Thr Asp Phe Ser Gly Ile Arg Asn Ile Ser Phe Met
            260                 265                 270

Val Lys Arg Ile Arg Ile Asn Thr Thr Ser Asp Glu Lys Asp Pro Thr
        275                 280                 285

Asn Pro Phe Arg Phe Pro Asn Ile Gly Val Glu Lys Phe Leu Glu Leu
    290                 295                 300

Asn Ser Glu Gln Asn His Asp Asp Tyr Cys Leu Ala Tyr Val Phe Thr
305                 310                 315                 320

Asp Arg Asp Phe Asp Asp Gly Val Leu Gly Leu Ala Trp Val Gly Ala
                325                 330                 335

Pro Ser Gly Ser Ser Gly Gly Ile Cys Glu Lys Ser Lys Leu Tyr Ser
            340                 345                 350

Asp Gly Lys Lys Lys Ser Leu Asn Thr Gly Ile Ile Thr Val Gln Asn
        355                 360                 365

Tyr Gly Ser His Val Pro Pro Lys Val Ser His Ile Thr Phe Ala His
    370                 375                 380

Glu Val Gly His Asn Phe Gly Ser Pro His Asp Ser Gly Thr Glu Cys
385                 390                 395                 400

Thr Pro Gly Glu Ser Lys Asn Leu Gly Gln Lys Glu Asn Gly Asn Tyr
```

```
                        405                 410                 415
Ile Met Tyr Ala Arg Ala Thr Ser Gly Asp Lys Leu Asn Asn Asn Lys
                420                 425                 430

Phe Ser Leu Cys Ser Ile Arg Asn Ile Ser Gln Val Leu Glu Lys Lys
            435                 440                 445

Arg Asn Asn Cys Phe Val Glu Ser Gly Gln Pro Ile Cys Gly Asn Gly
450                 455                 460

Met Val Glu Gln Gly Glu Cys Asp Cys Gly Tyr Ser Asp Gln Cys
465                 470                 475                 480

Lys Asp Asp Cys Cys Phe Asp Ala Asn Gln Pro Glu Gly Lys Lys Cys
                485                 490                 495

Lys Leu Lys Pro Gly Lys Gln Cys Ser Pro Ser Gln Gly Pro Cys Cys
            500                 505                 510

Thr Ala Gln Cys Ala Phe Lys Ser Lys Ser Glu Lys Cys Arg Asp Asp
        515                 520                 525

Ser Asp Cys Ala Lys Glu Gly Ile Cys Asn Gly Phe Thr Ala Leu Cys
530                 535                 540

Pro Ala Ser Asp Pro Lys Pro Asn Phe Thr Asp Cys Asn Arg His Thr
545                 550                 555                 560

Gln Val Cys Ile Asn Gly Gln Cys Ala Gly Ser Ile Cys Glu Lys Tyr
                565                 570                 575

Asp Leu Glu Glu Cys Thr Cys Ala Ser Ser Asp Gly Lys Asp Asn Lys
            580                 585                 590

Glu Leu Cys His Val Cys Cys Met Lys Met Ala Pro Ser Thr Cys
        595                 600                 605

Ala Ser Thr Gly Ser Leu Gln Trp Ser Lys Gln Phe Ser Gly Arg Thr
610                 615                 620

Ile Thr Leu Gln Pro Gly Ser Pro Cys Asn Asp Phe Arg Gly Tyr Cys
625                 630                 635                 640

Asp Val Phe Met Arg Cys Arg Leu Val Asp Ala Asp Gly Pro Leu Ala
                645                 650                 655

Arg Leu Lys Lys Ala Ile Phe Ser Pro Gln Leu Tyr Glu Asn Ile Ala
            660                 665                 670

Glu Trp Ile Val Ala His Trp Trp Ala Val Leu Leu Met Gly Ile Ala
        675                 680                 685

Leu Ile Met Leu Met Ala Gly Phe Ile Lys Ile Cys Ser Val His Thr
690                 695                 700

Pro Ser Ser Asn Pro Lys Leu Pro Pro Pro Lys Pro Leu Pro Gly Thr
705                 710                 715                 720

Leu Lys Arg Arg Arg Pro Pro Gln Pro Ile Gln Gln Pro Pro Arg Gln
                725                 730                 735

Arg Pro Arg Glu Ser Tyr Gln Met Gly His Met Arg Arg
            740                 745
```

(2) INFORMATION FOR SEQ ID NO: 9:

(i) SEQUENCE CHARACTERISTICS:
        (A) LENGTH: 486 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

TACAGCGACC AATGTAAGGA TGAATGTTGC TATGATGCCA ATCAGCCAGA AAACCTAAAG    60

-continued

```
TGCACATTAA AGCCTGGAAA ACAGTGCAGT CCCAGCCAGG GCCCTTGTTG CACCACTGGA      120

TGTACCTTCA AGCGAGCAGG TGAGAACTGT CGGGAGGAAT CTGACTGTGC CAAGATGGGA      180

ACTTGCAATG GCAACTCTGC TCAGTGTCCA CCATCCGAAC CAAGAGAGAA CCTGACTGAG      240

TGTAACAGGG CAACCCAAGT TTGCATCAAG GGGCAATGCT CAGGATCTAT CTGTGAGAGG      300

TATGACTTGG AAGAGTGCAC TTGCGGCAGT ACTGATGAAA AAGATGACAA AGAGCTGTGC      360

CACGTTTGCT GCATGGAGAA AATGATACCG CACACATGTG CTAGCACTGG TTCAGAAGTA      420

TGGAAAGCTT ACTTTAAAGG AAAGACTATT ACGTTACAAC CAGGATCACC TTGCAATGAA      480

TTTAAA                                                                 486
```

(2) INFORMATION FOR SEQ ID NO: 10:

(i) SEQUENCE CHARACTERISTICS:
        (A) LENGTH: 162 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Tyr Ser Asp Gln Cys Lys Asp Glu Cys Cys Tyr Asp Ala Asn Gln Pro
1               5                   10                  15

Glu Asn Leu Lys Cys Thr Leu Lys Pro Gly Lys Gln Cys Ser Pro Ser
            20                  25                  30

Gln Gly Pro Cys Cys Thr Thr Gly Cys Thr Phe Lys Arg Ala Gly Glu
        35                  40                  45

Asn Cys Arg Glu Glu Ser Asp Cys Ala Lys Met Gly Thr Cys Asn Gly
    50                  55                  60

Asn Ser Ala Gln Cys Pro Pro Ser Glu Pro Arg Glu Asn Leu Thr Glu
65                  70                  75                  80

Cys Asn Arg Ala Thr Gln Val Cys Ile Lys Gly Gln Cys Ser Gly Ser
                85                  90                  95

Ile Cys Glu Arg Tyr Asp Leu Glu Glu Cys Thr Cys Gly Ser Thr Asp
            100                 105                 110

Glu Lys Asp Asp Lys Glu Leu Cys His Val Cys Met Glu Lys Met
        115                 120                 125

Ile Pro His Thr Cys Ala Ser Thr Gly Ser Glu Val Trp Lys Ala Tyr
    130                 135                 140

Phe Lys Gly Lys Thr Ile Thr Leu Gln Pro Gly Ser Pro Cys Asn Glu
145                 150                 155                 160

Phe Lys
```

KUZ, A NOVEL FAMILY OF METALLOPROTEASES

This application is a divisional of U.S. Ser. No. 09/285,502, filed Apr. 2, 1999, now U.S. Pat. No. 6,190,876 which is a divisional of U.S. Ser. No. 08/937,931, filed Aug. 27, 1997, U.S. Pat. No. 5,935,792, which claims priority to U.S. Provisional Application Serial No. 60/019,390 filed Aug. 29, 1996 and to U.S. Provisional Application Serial No. 60/053,476 filed Jul. 23, 1997, each of which is incorporated by reference herein in its entirety.

FIELD OF THE INVENTION

The field of the invention is a novel family of proteins and genes involved in development.

BACKGROUND OF THE INVENTION

Cell-cell interactions play an important role in regulating cell fate decisions and pattern formation during the development of multicellular organisms. One of the evolutionarily conserved pathways that plays a central role in local cell interactions is mediated by the transmembrane receptors encoded by the Notch (N) gene of Drosophila, the lin-12 and glp-1 genes of C. elegans, and their vertebrate homologs (reviewed in Artavanis-Tsakonas, S., et al. (1995) Notch Signaling. Science 268, 225–232). collectively hereinafter referred to as NOTCH receptors. Several lines of evidence suggest that the proteolytic processing of NOTCH receptors is important for their function. For example, in addition to the full length proteins, antibodies against the intracellular domains of NOTCH receptors have detected C-terminal fragments of 100–120 kd (hereafter referred to as 100 kd fragments); see e.g. Fehon, R. G., et al. (1990). Cell 61, 523–534; Crittenden, S. L., et al. (1994). Development 120, 2901–2911; Aster, J., et al. (1994) Cold Spring Harbor Symp. Quant. Biol. 59, 125–136; Zagouras, P., et al.(1995). Proc. Natl. Acad. Sci. USA 92, 6414–6418; and Kopan, R., et al. (1996). Proc. Natl. Acad. Sci. USA 93, 1683–1688. However, the mechanism(s) of NOTCH activation have been hitherto largely unknown.

During neurogenesis, a single neural precursor is singled out from a group of equivalent cells through a lateral inhibition process in which the emerging neural precursor cell prevents its neighbors from taking on the same fate (reviewed in Simpson, P. (1990). Development 109, 509–519). Genetic studies in Drosophila have implicated a group of "neurogenic genes" including N in lateral inhibition. Loss-of-function mutations in any of the neurogenic genes result in hypertrophy of neural cells at the expense of epidermis (reviewed in Campos-Ortega, J. A. (1993) In: *The Development of Drosophila melanogaster* M. Bate and A. Martinez-Arias, eds. pp. 1091–1129. Cold Spring Harbor Press.). We disclose herein a new neurogenic gene family, kuzbanian (kuz) (Rooke, J., Pan, D. J., Xu, T. and Rubin, G. M. (1996). Science 273, 1227–1231). Members of the disclosed KUZ family of proteins are shown to belong to the recently defined ADAM family of transmembrane proteins, members of which contain both a disintegrin and metalloprotease domain (reviewed in Wolfsberg, T. G., et al. (1995). J. Cell Biol. 131, 275–278, see also Blobel, C. P., et al. (1992). Nature 356, 248–252, 1992; Yagami-Hiromasa, T., et al. (1995). Nature 377, 652–656; Black, R. A., et al. (1997). Nature 385, 729–733, 1997; and Moss, M. L., et al. (1997). Nature 385, 733–736).

We further disclose herein various engineered mutant forms of native KUZ proteins and their activities. We show that mutant KUZ proteins lacking protease activity interfere with endogenous KUZ activity and function as dominant negatives (indicating that the protease activity of native KUZ is essential to its biological functions) and that dominant negatives can perturb lateral inhibition during neurogenesis and result in the overproduction of primary neurons. We also show that proteolytic processing of NOTCH in embryos to generate the 100 kd species fails to occur in the kuz mutant embryo and expression of dominant negatives in imaginal discs or tissue culture cells blocks NOTCH processing (indicating that the primary NOTCH translation product is proteolytically cleaved by native KUZ proteins as part of the normal biosynthesis of a functional NOTCH receptor).

SUMMARY OF THE INVENTION

The invention provides methods and compositions relating to isolated KUZ polypeptides, related nucleic acids, polypeptide domains thereof having KUZ-specific structure and activity and modulators of KUZ function, particularly Notch protease activity. KUZ polypeptides, nucleic acids and modulators thereof regulate Notch signal transduction pathways and hence provide important regulators of cell function. The polypeptides may be produced recombinantly from transformed host cells from the subject KUZ polypeptide encoding nucleic acids or purified from mammalian cells. The invention provides isolated KUZ hybridization probes and primers capable of specifically hybridizing with the disclosed KUZ genes, KUZ-specific binding agents such as specific antibodies, and methods of making and using the subject compositions in diagnosis (e.g. genetic hybridization screens for KUZ transcripts), therapy (e.g. KUZ protease inhibitors to modulate Notch signal transduction) and in the biopharmaceutical industry (e.g. as immunogens, reagents for isolating additional natural kuz alleles, reagents for screening bio/chemical libraries for ligands and lead and/or pharmacologically active agents, etc.).

DETAILED DESCRIPTION OF PREFERRED EMBODIMENTS

Figure 1:
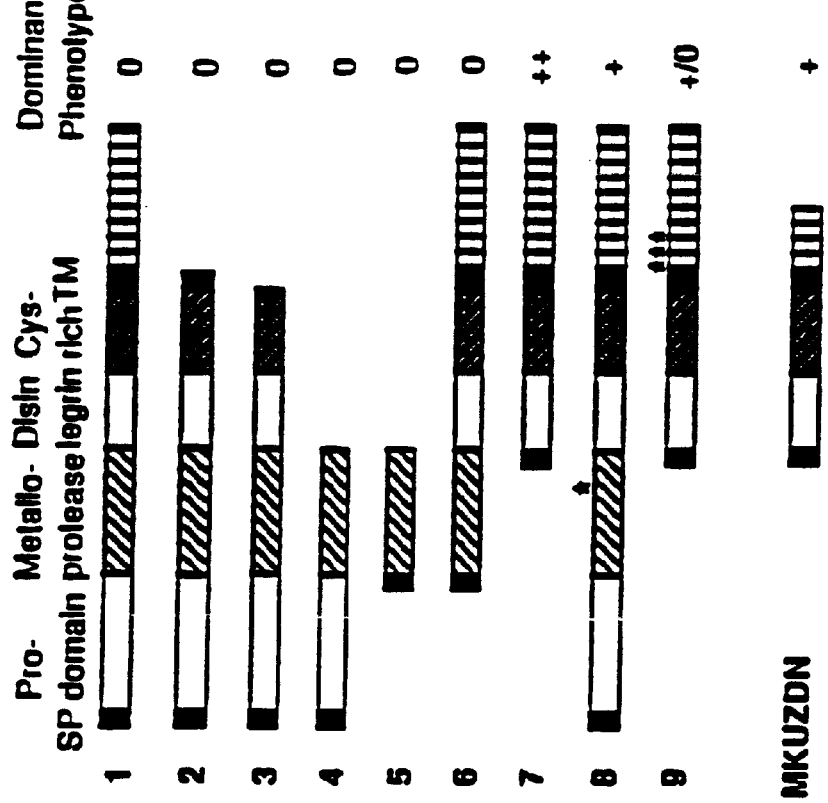
FIG. 1(A). Sequence alignment of predicted KUZ proteins from Drosophila (DKUZ, SEQ ID NO:2), mouse (MKUZ, SEQ ID NO:8) and Xenopus (XKUZ, SEQ ID NO:10). The full length amino acid sequence of MKUZ was deduced from the nucleotide sequence of two overlapping cDNA clones. Partial amino acid sequence of XKUZ was deduced from the nucleotide sequence of a PCR product that includes parts of the disintegrin and Cys-rich domains. The alignments were produced using Geneworks software (IntelliGenetics). Residues identical among two species are highlighted. Predicted functional domains are indicated. Amino acid sequences from which degenerate PCR primers were designed are indicated with arrows. Orthologs of kuz are also present in C. elegans (GenBank accession nos. D68061 and M79534), rat (Z48444), bovine (Z21961) and human (Z48579).
FIG. 1(B). Summary of constructs used in this study and their overexpression phenotypes. Different domains are indicated by shadings. Asterisks indicate where point mutations were introduced. Constructs 1–9 are based on DKUZ, while MKUZDN is based on MKUZ. Abbreviations: ++, strong phenotype; +, weak phenotype; 0, no phenotype.
FIG. 1(C). Schematic diagram of DKUZ, MKUZ and XKUZ. The percentages given refer to sequence identity in the indicated domains between MKUZ and either DKUZ or XKUZ.

The present invention provides isolated KUZ polypeptides, isolated from a wide variety of sources including Drosophila, human, mouse and Xenopus, as well as allelic variants, naturally occurring and altered secreted forms, deletion mutants having KUZ-specific sequence and/or bioactivity and mutants comprising conservative amino acid substitutions. SEQ ID NOS:1, 3, 5, 7 and 9 depict exemplary natural cDNAs encoding Drosphila, human transmembrane, human soluble (lacking a transmembrane domain), mouse and Xenopus members, respectively, of the disclosed KUZ family. SEQ ID NOS:2, 4, 6, 8 and 10 depict the corresponding encoded full-length KUZ proteins. Methods used to isolate additional members of the kuz family are described below and in the Examples.

Preferred translates/deletion mutants comprise at least a 10, preferably at least a 15, more preferably at least a 20 residue domain of at least one of SEQ ID NOS:2, 4, 6, 8 and 10. In particular, KUZ derivatives can be made by altering KUZ sequences by substitutions, additions or deletions that provide for functionally equivalent molecules. Due to the degeneracy of nucleotide coding sequences, other DNA sequences which encode substantially the same amino acid sequence as a kuz gene may be used in the practice of the present invention. These include but are not limited to nucleotide sequences comprising all or portions of kuz genes which are altered by the substitution of different codons that encode a functionally equivalent amino acid residue within the sequence, thus producing a silent change. Likewise, the KUZ derivatives of the invention include, but are not limited to, those containing, as a primary amino acid sequence, all or part of the amino acid sequence of a KUZ protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Conservative substitutes for an amino acid within the sequence may be selected from other members of the class to which the amino acid belongs. For example, the nonpolar (hydrophobic) amino acids include alanine, leucine, isoleucine, valine proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

In a specific embodiment of the invention, proteins consisting of or comprising a fragment of a KUZ protein consisting of at least 10 (continuous) amino acids of the KUZ protein is provided. In other embodiments, the fragment consists of at least 15 or 20 or 50 amino acids of the KUZ protein. In specific embodiments, such fragments are not larger than 35, 100 or 200 amino acids. Derivatives or analogs of KUZ include but are not limited to those peptides which are substantially homologous to a KUZ protein or fragments thereof. (e.g., at least 30%, 50%, 70%, or 90% identity over an amino acid sequence of identical size—e.g, comprising a domain) or whose encoding nucleic acid is capable of hybridizing to a coding KUZ sequence.

Ordinarily, the allelic variants, the conservative substitution variants and the members of the kuz family of proteins, will have an amino acid sequence having at least 75% amino acid sequence identity with one or more of the disclosed human full length, human secreted form, mouse and Drosophila kuz protein sequences, more preferably at least 80%, even more preferably at least 90%, and most preferably at least 95%. Identity or homology with respect to such sequences is defined herein as percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Figure 1C:
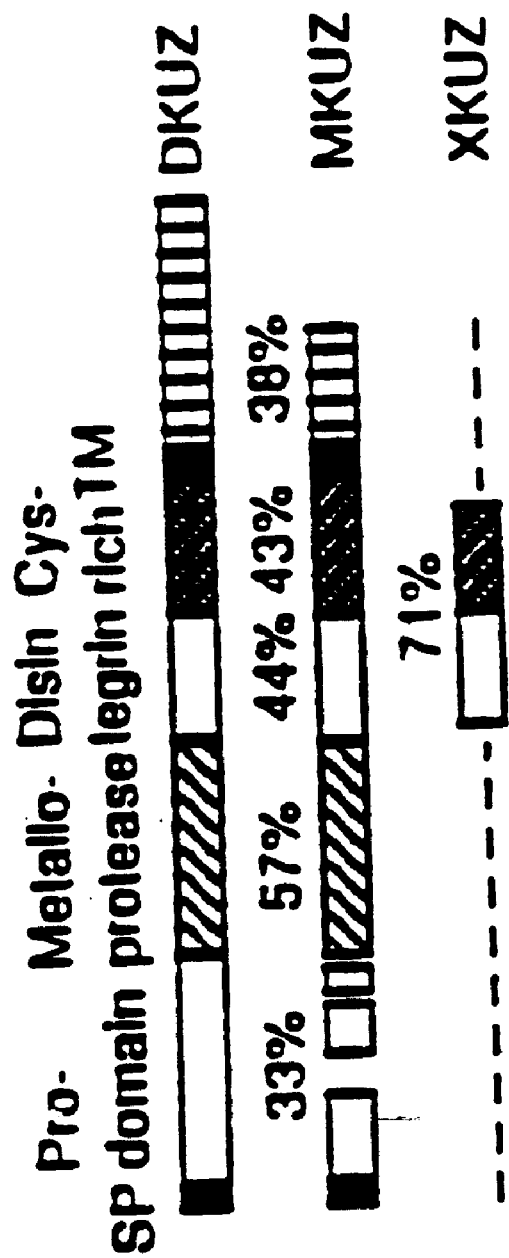

The subject domains provide KUZ domain specific activity or function, such as KUZ-specific protease or protease inhibitory activity, disintegrin or disintegrin inhibitory activity, ligand/antibody binding or binding inhibitory, immunogenicity, etc.; see, e.g. domains identified in FIGS. 1A–C. Preferred domains cleave a NOTCH protein. KUZ-specific activity or function may be determined by convenient in vitro, cell-based, or in vivo assays: e.g. in vitro binding assays, cell culture assays, in animals (e.g. gene therapy, transgenics, etc.), etc. Binding assays encompass any assay where the molecular interaction of an KUZ polypeptide with a binding target is evaluated. The binding target may be a natural intracellular binding target such as an KUZ substrate, a KUZ regulating protein or other regulator that directly modulates KUZ activity or its localization; or non-natural binding target such a specific immune protein such as an antibody, or an KUZ specific agent such as those identified in screening assays such as described below. KUZ-binding specificity may assayed by protease activity or binding equilibrium constants (usually at least about $10^7 M^{-1}$, preferably at least about $10^8 M^{-1}$, more preferably at least about $10^9 M^{-1}$), by the ability of the subject polypeptide to function as negative mutants in KUZ-expressing cells, to elicit KUZ specific antibody in a heterologous host (e.g a rodent or rabbit), etc. The KUZ binding specificity of preferred KUZ polypeptides necessarily distinguishes that of the bovine protein of Howard, L., et al. (1996). Biochem. J. 317,45–50.

The claimed KUZ polypeptides are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The KUZ polypeptides and polypeptide domains may be synthesized, produced by recombinant technology, or purified from mammalian, preferably human cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al, Greene Publ. Assoc., Wiley-Interscience, NY) or that are otherwise known in the art. Material and methods for the expression of heterologous recombinant proteins in bacterial cells (e.g. E. coli), yeast (e.g. S.

Cerevisiae), animal cells (e.g. CHO, 3T3, BHK, baculovirus-compatible insect cells, etc.). The KUZ polypeptides and/or domains thereof may be provided uncomplexed with other protein, complexed in a wide variety of non-covalent associations and binding complexes, complexed covalently with other KUZ or non-KUZ peptide sequences (homo or hetero-chimeric proteins), etc.

The invention provides binding agents specific to the claimed KUZ polypeptides, including substrates, agonists, antagonists, natural intracellular binding targets, etc., methods of identifying and making such agents, and their use in diagnosis, therapy and pharmaceutical development. For example, specific binding agents are useful in a variety of diagnostic and therapeutic applications, especially where disease or disease prognosis is associated with improper utilization of a pathway involving the subject proteins. Novel KUZ-specific binding agents include KUZ-specific receptors, such as somatically recombined polypeptide receptors like specific antibodies or T-cell antigen receptors (see, e.g Harlow and Lane (1988) Antibodies, A Laboratory Manual, Cold Spring Harbor Laboratory) and other natural intracellular binding agents identified with assays such as one-, two- and three-hybrid screens, non-natural intracellular binding agents identified in screens of chemical libraries such as described below, etc. Agents of particular interest modulate KUZ function, e.g. KUZ-dependent proteolytic processing. For example, a wide variety of inhibitors of KUZ Notch protease activity may be used to regulate signal transduction involving Notch. Metalloprotease and disintegrin inhibitors and methods for designing such inhibitors are well known in the art, e.g. Matrisian, L. TIG, 6:(1990), Hooper, N. FEBS Let. 354:1–6 (1994), Haas et al., Cur. Op. Cell Bio. 6:656–662 (1994), etc. Exemplary inhibitors include known classes of metalloprotease inhibitors, KUZ-derived peptide inhibitors, esp. dominant negative deletion mutants, etc. KUZ specificity and activity are readily quantified in high throughput protease assays using panels of proteases.

Accordingly, the invention provides methods for modulating signal transduction involving Notch in a cell comprising the step of modulating KUZ protease activity, e.g. by contacting the cell with a protease inhibitor. The cell may reside in culture or in situ, i.e. within the natural host. For use in methods applied to cells in situ, the compositions frequently further comprise a physiologically acceptable excipient and/or other pharmaceutically active agent to form pharmaceutically acceptable compositions. Hence, the invention provides administratively convenient formulations of the compositions including dosage units which may be incorporated into a variety of containers. The subject methods of administration generally involve contacting the cell with or administering to the host an effective amount of the subject compounds or pharmaceutically acceptable compositions. The compositions and compounds of the invention and the pharmaceutically acceptable salts thereof can be administered to a host in any effective way such as via oral, parenteral or topical routes. Preferred inhibitors are orally active in mammalian hosts.

In one embodiment, the invention provides the subject compounds combined with a pharmaceutically acceptable excipient such as sterile saline or other medium, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include solid, semi-solid or liquid media including water and non-toxic organic solvents.

In another embodiment, the invention provides the subject compounds in the form of a pro-drug, which can be metabolically converted to the subject compound by the recipient host. A wide variety of pro-drug formulations are known in the art. The compositions may be provided in any convenient form including tablets, capsules, lozenges, troches, hard candies, powders, sprays, creams, suppositories, etc. As such the compositions, in pharmaceutically acceptable dosage units or in bulk, may be incorporated into a wide variety of containers. For example, dosage units may be included in a variety of containers including capsules, pills, etc.

The compositions may be advantageously combined and/or used in combination with other therapeutic or prophylactic agents, different from the subject compounds. In many instances, administration in conjunction with the subject compositions enhances the efficacy of such agents, see e.g. *Goodman & Gilman's The Pharmacological Basis of Therapeutics*, 9$^{th}$ Ed., 1996, McGraw-Hill. For diagnostic uses, the inhibitors or other KUZ binding agents are frequently labeled, such as with fluorescent, radioactive, chemiluminescent, or other easily detectable molecules, either conjugated directly to the binding agent or conjugated to a probe specific for the binding agent.

According to the invention, a KUZ protein, its fragments or other derivatives, or analogs thereof, may be used as an immunogen to generate antibodies which recognize such an immunogen. Such antibodies include but are not limited to polyclonal, monoclonal, chimeric, single chain, Fab fragments, and an Fab expression library. In a specific embodiment, antibodies to human KUZ are produced. In another embodiment, antibodies to the extracellular domain of KUZ are produced. In another embodiment, antibodies to the intracellular domain of KUZ are produced.

Various procedures known in the art may be used for the production of polyclonal antibodies to a KUZ protein or derivative or analog. In a particular embodiment, rabbit polyclonal antibodies to an epitope of the KUZ protein encoded by a sequence selected from SEQ ID NOS:1, 3, 5, 7 or 9 or a subsequence thereof, can be obtained. For the production of antibody, various host animals can be immunized by injection with the native KUZ protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward a KUZ protein sequence or analog thereof, any technique which provides for the production of antibody molecules by continuous cell lines in culture may be used. For example, the hybridoma technique originally developed by Kohler and Milstein (1975, Nature 256: 495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal antibodies and Cancer Therapy, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci.

U.S.A. 80: 2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule specific for KUZ together with genes from a human antibody molecule of appropriate biological activity can be used; such antibodies are within the scope of this invention.

According to the invention, techniques described for the production of single chain antibodies (U.S. Pat. No. 4,946,778) can be adapted to produce KUZ-specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity for KUZ proteins, derivatives, or analogs.

Antibody fragments which contain the idiotype of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. In the production of antibodies, screening for the desired antibody can be accomplished by techniques known in the art e.g. ELISA (enzyme-linked immunosorbent assay). For example, to select antibodies which recognize a specific domain of a KUZ protein, one may assay generated hybridomas for a product which binds to a KUZ fragment containing such domain. For selection of an antibody immunospecific to human KUZ, one can select on the basis of positive binding to human KUZ and a lack of binding to a KUZ of another species. The foregoing antibodies can be used in methods known in the art relating to the localization and activity of the protein sequences of the invention, e.g., for imaging these proteins, measuring levels thereof in appropriate physiological samples, in diagnostic methods, etc. Antibodies specific to a domain of a KUZ protein are also provided. In a specific embodiment, antibodies which bind to a Notch-binding fragment of KUZ are provided.

The amino acid sequences of the disclosed KUZ polypeptides are used to back-translate KUZ polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural KUZ-encoding nucleic acid sequences ("GCG" software, Genetics Computer Group, Inc, Madison Wis.). KUZ-encoding nucleic acids used in KUZ-expression vectors and incorporated into recombinant host cells, e.g. for expression and screening, transgenic animals, e.g. for functional studies such as the efficacy of candidate drugs for disease associated with KUZ-modulated cell function, etc.

The invention also provides nucleic acid hybridization probes and replication/amplification primers having a KUZ cDNA specific sequence comprising SEQ ID NO:1, 3, 5, 7 or 9, and sufficient to effect specific hybridization thereto (i.e. specifically hybridize with SEQ ID NO:1, 3, 5, 7 or 9, respectively, in the presence of an embryonic cDNA library from the corresponding species, and preferably in the presence of BMP cDNA as described by Howard and Glynn (1995). Such primers or probes are at least 12, preferably at least 24, more preferably at least 36 and most preferably at least 96 bases in length. Demonstrating specific hybridization generally requires stringent conditions, i.e. those that (1) employ low ionic strength and high temperature for washing, for example, 0.015 M NaCl/0.0015 M sodium titrate/0.1% SDS at 50° C., or (2) employ during hybridization a denaturing agent such as formamide, for example, 50% (vol/vol) formamide with 0.1% bovine serum albumin/ 0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 (g/ml), 0. 1% SDS, and 10% dextran sulfate at 42° C., with washes at 42° C. in 0.2×SSC and 0.1% SDS. KUZ nucleic acids can also be distinguished using alignment algorithms, such as BLASTX (Altschul et al. (1990) Basic Local Alignment Search Tool, J Mol Biol 215, 403–410).

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising the nucleotide sequence of SEQ ID NO:1, 3, 5, 7 or 9, or the subject fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, knock-in/out vectors, hybridization probes, PCR primers, diagnostic nucleic acids, etc.; use in detecting the presence of KUZ genes and gene transcripts and in detecting or amplifying nucleic acids encoding additional KUZ homologs and structural analogs. In diagnosis, KUZ hybridization probes find use in identifying wild-type and mutant KUZ alleles in clinical and laboratory samples. Mutant alleles are used to generate allele-specific oligonucleotide (ASO) probes for high-throughput clinical diagnoses. In therapy, therapeutic KUZ nucleic acids are used to modulate cellular expression or intracellular concentration or availability of active KUZ.

The invention provides efficient methods of identifying agents, compounds or lead compounds for agents active at the level of a KUZ modulatable cellular function. Generally, these screening methods involve assaying for compounds which modulate KUZ interaction with a natural KUZ binding target such as a Notch protein, etc. A wide variety of assays for binding agents are provided including labeled in vitro protein-protein binding assays including protease assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

Exemplary in vitro binding assays employ a mixture of components including an KUZ polypeptide, which may be part of a fusion product with another peptide or polypeptide, e.g. a tag for detection or anchoring, etc. The assay mixtures comprise a natural intracellular KUZ binding target. In a particular embodiment, the binding target is a Notch protein-derived substrate of KUZ protease activity. Such substrates comprise a specifically KUZ-cleavable peptide bond and at least 5, preferably at least 10, and more preferably at least 20 naturally occurring immediately flanking residues on each side. While native full-length binding targets may be used, it is frequently preferred to use portions (e.g. peptides) thereof so long as the portion provides binding affinity and avidity to the subject KUZ polypeptide conveniently measurable in the assay. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other M reagents may also be included in the mixture. These include reagents like ATP or ATP analogs (for protease assays), salts, buffers, neutral proteins, e.g. albumin, detergents, non-specific protease inhibitors, nuclease inhibitors, antimicrobial agents, etc. may be used.

The resultant mixture is incubated under conditions whereby, but for the presence of the candidate pharmacological agent, the KUZ polypeptide specifically binds the cellular binding target, portion or analog with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the KUZ polypeptide and one or more binding targets is detected by any convenient way. For KUZ protease assays, 'binding' is generally detected by the generation of a KUZ substrate cleavage product. In this embodiment, protease activity may quantified by the apparent transfer a label from the substrate to the nascent smaller cleavage product, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the KUZ polypeptide to the target in the absence of the agent as compared with the binding affinity in the presence of the agent indicates that the agent modulates the binding of the KUZ polypeptide to the KUZ binding target. Analogously, in cell-based assays described below, a difference in KUZ-dependent modulation of signal transduction in the presence and absence of an agent indicates the agent modulates KUZ function. A difference, as used herein, is statistically significant and preferably represents at least a 50%, more preferably at least a 90% difference.

Altered Drosophila hosts in which the kuz gene is over-expressed, under-expressed, mis-expressed or expressed as a variant are used to identify compounds that are antagonist or agonists of the KUZ polypeptide as well as to identify genes that encode products that interact with the KUZ polypeptide using art known methods (Xu et al., Genes and Devel., p464–475 (1990), Simon et al., Cell, 67:701–716 (1991) and Fortini et al., Cell, 79:273–282 (1994)).

Agents that modulate the interactions of the KUZ polypeptide with its ligands/natural binding targets can be used to modulate biological processes associated KUZ function, e.g. by contacting a cell comprising a KUZ polypeptide (e.g. administering to a subject comprising such a cell) with such an agent. Biological processes mediated by KUZ polypeptides include a wide variety of cellular events which are mediated when a KUZ polypeptide binds a ligand e.g. cell differentiation, cell development and neuronal partitioning. The agents are also used to modulate processes effected by KUZ substrates; for example, Notch, an art known peptide involved in neurogenesis is over-expressed in some forms of leukemia (Ellison et al., Cell, 66:649–661 (1991)).

The present invention further provides methods for identifying cells involved in KUZ polypeptide-mediated activity, e.g. by determining whether the KUZ polypeptide, or a kuz ligand, is expressed in a cell. Such methods are useful in identifying cells and events involved in neurogenesis. In one example, an extract of cells is prepared and assayed by of a variety of immunological and nucleic acid techniques to determine whether the KUZ polypeptide is expressed. The presence of the KUZ polypeptide provides a measurement of the participation or degree of neurogenesis of a cell.

The invention provides a wide variety of methods and compositions for evaluating modulators of the KUZ signaling pathways. For example, the invention provides transgenic non-human animals such as flies (e.g. Drosophila), worms (e.g. *C. elegans*), mice, etc. having at least one structurally and functionally disrupted KUZ allele. In particular embodiments, the animals comprise a transgene within a KUZ allele locus, encoding a selectable marker and displacing at least one exon of the KUZ allele. More particularly, the transgene may comprise 3' and 5' regions with sufficient complementarity to the natural KUZ allele at the locus to effect homologous recombination of the transgene with the KUZ allele. Such animals provide useful models for determining the effect of candidate drugs on a host deficient in KUZ function.

As describe above, the invention provides a wide variety of methods for making and using the subject compositions. As additional examples, the invention provides methods for determining the effect of a candidate drug on a host deficient in KUZ function, such as: contacting a transgenic animal having at least one disrupted KUZ allele with a candidate drug; and, detecting the presence or absence of a physiological change in the animal in response to the contacting step. The invention also provides methods of evaluating the side effects of a KUZ function inhibitor, such as: contacting a transgenic animal having at least one disrupted KUZ allele with a candidate drug; detecting the presence or absence of a physiological change in the animal in response to the contacting step, wherein the presence of a physiological change indicates the inhibitor has side effects beyond KUZ function inhibition.

Without further description, one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure. Other generic configurations will be apparent to one skilled in the art. All publications and patent applications cited in this specification are herein incorporated by reference as if each individual publication or patent application were specifically and individually indicated to be incorporated by reference.

EXAMPLES

Example 1
Identification of a Drosophila KUZ Polypeptide/Gene

Genes involved in lateral inhibition were screened using FLP/FRT chromosomes to produce mutant clones in mosaic animals (T. Xu and G. M. Rubin, Development 117:1223 (1993); T. Xu and S. Harrison *Methods in Cell Biology* 44:655 (1994)) and to isolate several alleles of a gene family designated herein as kuzbanian (kuz). The kuz locus is defined by a single complementation group which maps to chromosomal location 34C4,5, and corresponds to the 1(2) 34 Da group (A. C. Spradling et al., PNAS 92:10824 (1995). Most of the kuz phenotypic analysis was performed using the null allele kuze29-4. Kuze29-4 is an excision allele deleting approximately 2.4 kb at the 5' end of the kuz gene, including DNA in the promoter region and the first and second exons. Four P[lacZ; w+] insertions 1(2)k11804, 1(2)k01403, 1(2)k07601 and 1(2)k14701 are hypomorphic kuz alleles. The insert either in the first kuz exon or in the first intron. Precise excision of these P insertions reverts the associated kuz phenotype. Kuz1 is the original kuz allele caused by an insertion of 4.3 kb of DNA in or near the first exon. Seventeen additional X-ray induced kuz alleles were isolated in the FLP/FRT mosaic screen.

A 10 kb fragment of DNA from the region deleted in allele kuze29-4 was used to screen a Drosophila total imaginal disc cDNA library. A group of two overlapping 1.2 kb cDNAs mapping to this region was recovered; a full-length kuz cDNA, NB1, was isolated from an embryonic cDNA library using the small cDNA clones as probes (Kuz cDNA Genbank accession number: U60591).

Scanning electron microscopy (SEM) and embryo staining and adult eye sections were carried out following standard procedures (A. Tomlinson and D. F. Ready, *Dev. Biol.* 123:264 (1987); T. Xu and S. Artavanis-Tsakonas, *Genetics* 126, 665 (1990)). A scanning electron micrograph (SEM) showing the multiple bristle phenotype in an adult mosaic fly with homozygous kuz clones revealed that aeveral macro- and microchaete positions have supernumerary bristles whereas others are missing in the same area. SEMs showing kuz clones in the eye revealed the regular array of ommatidia is severely disrupted, that toward the center of the clone the density of photoreceptors is abnormally low and none are successfully organized into ommatidia, and that chimeric ommatidia at the clone border contain a mixture of pigmented wild-type photoreceptor cells and mutant, unpigmented photoreceptors. Confocal images of embryos stained with the neuronal-specific anti-Elav antibody demonstrate a requirement for maternal and zygotic kuz products. A kuz maternal null embryo (generated using the ovoD mutation as described in T. B. Chou and N. Perrimon, *Genetics* 131:643 (1992)) with one zygotic copy of kuz revealed that a greater proportion of the embryo developed as neural tissue than in wild-type and a surface view of a kuz null embryo with no maternal or zygotic kuz product showed that most cells adopted a neural fate. A lower focal plane of this same embryo showed that all cells around the periphery of the embryo are neural cells.

A cuticular preparation of a kuz maternal null embryo with one zygotic copy of kuz showed a small patch of cuticle develops on the dorsal side of the embryo; presumably the remaining cells which failed to produce cuticle adopted a neural fate, consistent with the previously phenotype. A cuticular preparation of a kuz null embryo showed only a tiny dot of cuticle developed. Most of these embryos show no cuticle at all.

Animals with kuz mutant clones exhibit clusters of sensory bristles at positions in which single sensory bristles are normally observed. Separate sockets are often seen with individual bristles, and stimulation of mutant bristles in a reflex test elicits a leg cleaning response, indicating that mutant clusters contain multiple sensory bristles and not just multiple shafts (P. Vandervorst and A. Ghysen, Nature 286:65 (1980)). This multiple bristle phenotype is observed in clones mutant for several neurogenic genes such as Notch (N) and shaggy (sgg, also known as zeste-white 3), and is indicative of a failure of lateral inhibition during the development of the peripheral nervous system (S. Artavanis-Tsakonas, et al., *Trends in Genetics* 7:403 (1991); J. S. Campos-Ortega (1993); Jan, Y. N. and Jan, L. Y., id., pp. 1207–1244; Romani, S. et al., *Genes Dev.* 3:997 (1989); Artavanis-Tsakonas, S. et al., *Science* 268:225 (1995); Heitzler, P. and Simpson, P. (1991). Cell 64, 1083–1092).

Unlike the N phenotype, kuz clones do not produce ectopic bristles, indicating kuz is not required for correct spacing between proneural clusters. Mutant clones in the adult eye severely disrupted the regular array of ommatidia. Thin sections through such a mosaic eye reveal that mutant photoreceptors are not organized correctly into ommatidia.

To determine whether the KUZ polypeptide is required for the development of the central nervous system (CNS), embryos lacking any maternally derived KUZ polypeptide and containing one or no zygotic copies of the kuz gene were produced. The embryos were examined by staining with neuronal-specific antibodies to the Elav protein (Bier, E. et aL, *Science* 240:913 (1988); Robinow, S. et al.,*J. Neurobiol.* 22, 443 (1991)). Maternal null embryos with one copy of zygotic kuz gene showed hyperplasia and disorganization of the CNS on the ventral side of the embryos, which is a phenotype similar to the neurogenic phenotype of N mutant embryos (Lehmann, R. et al., *Roux's Arch Dev. Biol.* 192:62 (1983)). However, embryos lacking all maternal and zygotic KUZ polypeptide have a much more severe neurogenic phenotype. Hypertrophy of the nervous system is not restricted to the ventral region, but the embryos stained throughout with anti-Elav, demonstrating that many more cells in the embryo had developed as neural cells. Such a severe neuralizing phenotype is similar to that of sgg null embryos (Bourouis, M. et al., *Nature* 341:442 (1989)). Cuticular preparation of embryos correlated well with the antibody results: Maternal-null embryos with one copy of the kuz gene produced a small patch of cuticle on the dorsal side, consistent with the observation that many of the ventral cells had adopted a neural fate at the expense of epidermis. Embryos with no KUZ polypeptide produced little or no cuticle, as would be expected if most cells had become neural, leaving few epidermal cells to secrete cuticle.

Further analyses on the development of adult sensory bristles were performed to determine a specific role for the KUZ polypeptide in lateral inhibition. The yellow (y) and crinkle (ck) marker mutations were used to mark kuz- clones in the adult cuticle. This allows one to determine the genotype of individual cells and thus to examine the autonomy of the kuz mutant phenotype. Such analysis can distinguish between sending and receiving roles for a gene involved in the lateral inhibition process (Heitzler, P. et al., *Cell* 64:1083 (1991)).

A role for the KUZ polypeptide in lateral inhibition is suggested by the observation that all sensory bristles in a mutant cluster are kuz-; no wild-type bristles are ever present in a cluster. SEM of kuz- clones (each kuz- cell is also ck- and y-) revealed that the ck- mutation results in extra trichomes in the epidermal cell and in blunted shafts of sensory bristles; these morphological changes allow the border between mutant and wild-type cells to be precisely determined. A marked absence of all micro- and macrochaetes is observed in the interior of the clone, as no shafts, sockets, or neurons (naked cells) are seen. Kuz- mutant cells at normal bristle positions do form bristles at clone borders where they are in contact with wild-type cells. A high-magnification view of one of the multiple macrochaete clusters at a clone border revealed that every bristle in this and other clusters is always ck- and y-, demonstrating that all bristles in a cluster are kuz-. No wild-type bristles are observed in multiple bristle clusters. Marked kuz- clones were generated iny- w- hsFLP1; kuse29-4 ck-P[FRT]40A/P[y+] P[w+]P[FRT]40A first instar larvae following protocols described in T. Xu and G. M. Rubin, Development 117:1223 (1993) and T. Xu and S. Harrison *Methods in Cell Biology* 44:655 (1994).

Mosaic analysis for kuz- clones in the adult cuticle indicates two distinct functions for the kuz protein. First, the failure of lateral inhibition, evidenced by the formation of extra bristles, only occurs in kuz- mutant cells. This cell-autonomous mutant phenotype indicates that during normal development, the kuz protein is required in cells to receive an inhibitory signal. kuz- cells at normal bristle-forming positions become bristles only when they are in contact with wild-type cells, indicating that in wild-type animals, the KUZ polypeptide may act as a positive signal or is involved in sending a positive signal for the development of the bristle. Thus, there is a cell-autonomous requirement for kuz in order for cells to be inhibited from adopting a neural precursor fate. We conclude that the KUZ polypeptide is required in cells to receive an inhibitory signal from the emerging neural cell. Cells in the proneural cluster with wild-type KUZ polypeptide function receive the inhibitory signal and are forced to become epidermal, whereas kuz- cells cannot be inhibited and develop as neural precursor cells. A second distinct role for the KUZ polypeptide was revealed by the same mosaic analyses. All mutant bristle clusters were produced at clone borders, where mutant cells contact wild-type cells. No bristles were ever produced in clone interiors, either singly or in clusters. Large kuz- clones therefore cause bare patches devoid of bristles containing only hair-secreting epidermal cells. This phenotype indicates there is a non cell-autonomous requirement for the KUZ polypeptide in bristle development. Hence, Kuz participates in both neural-promoting and -inhibiting processes during formation of the adult epidermis.

To reveal the molecular basis of the KUZ polypeptide functions, a kuz gene was cloned and a full-length cDNA was obtained. The kuz cDNA contained an open reading frame that encodes a1,239 amino acid membrane-spanning protein of the metalloprotease-disintegrin family known as the ADAM family (members of the ADAM family contain "A Disintegrin And Metalloprotease Domain". The KUZ metalloprotease domain also contains a conserved zinc-binding site (Jiang, W. and Bond, J. S. (1992). FEBS Letters 312, 110–114). Like other disintegrins KUZ has a characteristic spacing of cysteine residues that is required for their direct binding to receptors (Niewiarowski, S. et al., *Semi-nars in Hematology* 31:289 (1994)). These cysteines are conserved in the KUZ polypeptide along with many additional residues that are shared by other disintegrin domains. In this family, many proteins with a multi-domain structure are proteolytically processed to produce multiple peptides with different functions (Blobel, C. P. et aL, *J. Cell Biol.* 111:69 (1990); Neeper, M. P. et al., *Nucleic Acids Res.* 18:4255 (1990); Au, L. C., et al., *Biochem. Biophys. Res. Commun.* 181:585 (1991)). The metalloprotease and disintegrin domains of kuz may be cleaved from the full-length precursor to produce both soluble and membrane-bound forms of these domains. Such proteolytic products of the KUZ polypeptide may be used to carry out the different KUZ polypeptide functions.

Example 2

Identification of Two Human and One Mouse KUZ Polypeptides/genes.

The nucleic acid sequence of the Drosophila kuz gene was used to generate PCR primers for amplifying kuz encoding nucleic acid molecules from organisms other than Drosophila. A 0.9 kb cDNA fragment was amplified from a human fetal brain cDNA library (Clonetech, Stratagene) using PCR primers. This fragment was cloned and was used as a probe to screen the human fetal brain cDNA library (Clonetech, Stratagene). A clone containing a 3.5 kb insert was obtained (SEQ ID NO:3). The cloned contained a full length encoding sequence that encodes a protein of 749 amino acids. Three additional clones were obtained that showed variant restriction digestion patterns. Sequence analysis of these clones identified a second form of the human KUZ polypeptide. This second form of the KUZ polypeptide encodes a protein of 330 amino acids in length (SEQ ID NO:6). A fragment of the human kuz encoding sequence was used to probe a mouse fetal brain cDNA library. One of four isolated clones was sequenced and contained a 4 kb insert representing a murine KUZ cDNA (SEQ ID NO:7).

Northern blots run using RNA isolated from various mouse and human tissues revealed expression in fetal and adult tissues. Hybridization of the blots with probes specific to each of the human forms confirmed that each of the transcripts was unique to one of the two forms, indicating that the two identified mRNA transcripts represent each of the two human forms respectively. The variable pattern of expression seen on the adult and fetal Northern blots indicates a developmental role of the KUZ polypeptides: the short form being predominant in adult tissues while the full lebgth form is predominant in fetal tissues and adult brain. All regions of the adult brain expressed both forms.

Example 3

KUZBANIAN Control Proteolytic Processing of NOTCH and Mediates Lateral Inhibition During Drosophila and Vertebrate Neurogenesis.

To investigate how the different domains of KUZ contribute to its biological functions, full length and various N- and C-terminal truncations of KUZ were generated (e.g. constructs 1–4 and 7, FIG. 1B) and expressed under the pGMR vector (hay, B. A., Wolff, T. and Rubin, G. M. (1994). Development 120, 2121–2129) in the developing retina of Drosophila. One of these exemplary truncations (7), which is missing the protease domain, resulted in a dominant rough eye phenotype. We expressed KUZ truncations using the pDMR vector which contains the decapentaplegic (dpp) dixc specific enhancer element (see experimental procedures) that drives gene expression in several tissues including parts of the notum and the wing blade, two tissues that are known to be affected in kuz mutant clones. Expression of construct 7 under pDMR resulted in supernumerary bristles on the notums and notches on the wing blades. These phenotypes resemble those seen in somatic clones homozygous for kuz loss-of-function mutations, indicating that this construct functions in a dominant negative manner by interfering with endogenous kuz activity. We also observed that the mutant phenotypes resulting from this construct are dominantly enhanced by removing one copy of the endogenous kuz gene; that is, the phenotypes of kuz/+ individuals carrying this construct are more severe than those of +/+ individuals. Conversely, additional wildtype KUZ protein from a transgene expressing full length KUZ suppresses these phenotypes. We refer to the particular dominant negative of construct 7 hereafter as KUZDN (KUZ dominant negative).

To directly address the functional relevance of the protease domain, we introduced into full length KUZ a point mutation (E606 to A) in the putative zinc binding site (FIG. 1A) of the protease domain. This glutamate is thought to be a catalytic residue and is absolutely conserved among all known metalloproteases (Jiang and Bond, 1992). Thus, this point mutation should abolish protease activity while having minimal impact on the other activities of KUZ. Indeed, overexpression of $KUZ^{E606A}$ (construct 8 in FIG. 1B) gave similar, although somewhat weaker, dominant phenotypes to those seen with KUZDN.

The notums of Drosophila adults carry two types of sensory bristles, macrochaetes and microchaetes. The sensory organ precursor cells (SOPs) that generate the macrochaetes are selected from pools of equivalent cells by lateral inhibition mostly during the third instar larval stage, while the SOPs for the microchaetes are singled out during the early pupae stage (Huang, F., et al. (1991). Development 111, 1087–1095; Hartenstein, V. and Posakony, J. W. (1989). Development 107, 389–405). N is required for this process and removal of N function at larval and pupal stages differentially affects these two types of bristles (Hartenstein, V. and Posakony, J. W. (1990). Dev. Biol. 142, 13–30). If KUZ is required for lateral inhibition, we would expect to generate similar phenotypes by expressing KUZDN at these times. We generated flies containing KUZDN under the control of the hsp70 promoter, and applied one hour heat pulses at various times during larval and pupal development. We observed that while heat pulses applied during third instar larval stage resulted in supernumerary macrochaetes only, heat pulses applied during early pupal stages (0–13 hrs after puparium formation (APF)) resulted in supernumerary microchaetes only, similar to the phenotypes resulted from removing N function at these times using a temperature sensitive N allele (Hartenstein and Posakony, 1990). These time points match the periods when SOPs for each bristle type are selected from pools of equivalent cells (Huang et al., 1991; Hartenstein and Posakony, 1989), indicating that KUZDN interferes with lateral inhibition during the selection of SOPs.

Kuz mutant clones affect other tissues such as the eye. We perturbed kuz functions by expressing KUZDN under the control of the rough enhancer, which drives gene expression in all cells within the morphogenetic furrow as well as transiently in R2, R5, R3 and R4 posterior to the furrow (Heberlein, U., et al. (1994). Mech. Dev. 48, 35–49). Flies carrying the rough/KUZDN transgene had supernumerary photoreceptor cells in each ommatidium. Neuronal differentiation in these transgenic flies was followed by staining for ELAV, a neuronal marker, in eye imaginal discs. Consistent with the adult eye phenotype, we observed the recruitment of extra neurons into each ommatidial cluster in the developing retina. These experiments indicate that kuz function is required to limit the number of photoreceptor neurons recruited into each ommatidium.

Besides its flnctions in determining neural fate, kuz is also required for axonal extension at later stages of neural development (Fambrough, D., et al. (1996). Proc. Natl. Acad. Sci. USA 93, 13233–13238). We expressed KUZDN under the control of the ELAV promoter using the GAL4-UAS system (Brand, A. H., and Perrimon, N. (1993). Development 118, 401–415). The ELAV promoter drives gene expression in maturing and mature neurons, but not neuroblasts, thus allowing one to bypass the requirement for kuz in neural fate determination. We observed that embryos expressing KUZDN in developing neurons show major defects in axonal pathways, such as disruption of longitudinal axonal tracts. In general, this phenotype is similar to the that observed in zygotic kuz mutant embryos (Fambrough et al., 1996), indicating that KUZ provides a proteolytic activity synthesized by axons and required by them to extend growth cones through the extracellular matrix.

Database searches revealed sequences representing putative kuz orthologs in C. elegans, rat, bovine and human. The bovine homolog was initially isolated as a proteolytic activity on myelin basic protein in vitro (Howard et al., 1996). We isolated and sequenced cDNAs representing a full-length mouse kuz homolog. This mouse protein (MKUZ) is 45% identical in primary sequence with Drosophila KUZ (DKUZ, FIG. 1), and 95% identical with the bovine protein. Sequence similarity between MKUZ and DKUZ extends over the whole coding region, except that MKUZ, like other vertebrate KUZ homologs, has a much shorter intracellular domain. The intracellular domain of MKUZ contains a stretch of 9 amino acid residues (934–942) that are absolutely conserved with DKUZ. To determine the functional importance of this sequence similarity, we introduced into KUZDN mutations in several conserved residues in this region (936TPSS939 to AAAA; construct 9 in FIG. 1B) and found these mutations dramatically reduced KUZDN activity.

Based on the structure of KUZDN described above, we engineered a dominant negative form of MKUZ (MKUZDN, FIG. 1B) missing the protease domain. When overexpressed in Drosophila using the pDMR vector, MKUZDN resulted in dominant phenotypes resembling those created by its Drosophila counterpart. To test directly the involvement of MKUZ in vertebrate neurogenesis, we injected in vitro transcribed mRNA encoding MKUZDN into Xenopus embryos. Primary neurons in Xenopus are generated in precise and simple patterns and can be identified by their expression of a neural specific β-tubulin gene (N-tubulin). This assay has been used previously to demonstrate a conserved role for certain neurogenic genes in singling out primary neurons in Xenopus by lateral inhibition (Chitnis, A., et al. (1995). Nature 375, 761–766). If a kuz-like activity is required for the lateral inhibition process in Xenopus, we would expect interference with this endogenous kuz activity to result in the overproduction of primary neurons. Indeed, injection of MRNA encoding MKUZDN resulted in extra N-tubulin positive cells. Consistent with the notion that kuz acts to limit the number of cells that differentiate as neurons from a group of competent cells, these extra N-tubulin positive cells were confined to domains of primary neurogenesis, and were not observed at ectopic positions.

To provide further evidence for an endogenous kuz activity during primary neurogenesis in Xenopus, we examined the expression pattern of a Xenopus kuz homolog (Xkuz). A cDNA fragment representing a portion of xkuz (FIG. 1) was isolated (see experimental procedures) and used to generate RNA probes for in situ hybridization under high stringency. Xkuz is expressed uniformly in gastrulating and neural plate stage embryos, including the domains of primary neurogenesis. In older embryos, Xkuz continues to be widely expressed, with an elevated level in neural tissues. Thus, Xkuz is expressed at the appropriate time and place for a potential role in primary neurogenesis in Xenopus.

We sought to determine the order of action of N and kuz by examining the phenotype produced by combining a gain-of-function N mutant and a loss-of-function kuz mutant. Expression of an activated form of NOTCH (reviewed in Artavanis-Tsakonas et al., 1995) under the heat shock promoter (hs-$N^{act}$) at early pupal stages (7–9 hours APF) leads to the loss of microchaetes on the notum; the opposite phenotype, extra microchaetes, is seen in loss-of-function kuz mutant clones. We focused on microchaetes since the SOPs for these bristles are generated more synchronously than those of the macrochaetes (Huang et al., 1991; Hartenstein and Posakony, 1989) and thus a single pulse of heatshock at 7–9 hrs APF results in the reproducible loss of microchaetes on the notum in hs-$N^{act}$ flies. If kuz acts genetically downstream of N, then the combination of $N^{act}$ and kuz should display the kuz phenotype of extra microchaetes. Conversely, if kuz acts genetically upstream of N, then the combination of $N^{act}$ and kuz should display the $N^{act}$ phenotype of missing microchaetes. We observed that the combination of $N^{act}$ and kuz displayed the $N^{act}$ phenotype, indicateing that kuz acts genetically upstream of N. This result indicates KUZ acts upstream of, or parallel with NOTCH in the same biochemical pathway.

We observed dosage sensitive genetic interactions between kuz and N, indicating that the levels of activity of kuz and N are tightly balanced. We took advantage of a weak dpp-KUZDN transgene that resulted in an average of 3 posterior scutellar bristles instead of the 2 seen in wildtype. While heterozygous N mutants have normal number of posterior scutellar bristles, this genetic background dramatically enhanced the phenotype resulting from the weak dpp-KUZDN transgene such that an average of 5.2 bristles (n=50) were observed. Furthermore, in flies that carry an additional copy of N gene, the extra bristle phenotype resulting from this KUZDN transgene is completely suppressed such that 2 bristles were observed. This intricate balance between their activities indicates that kuz and N are closely linked in a common biological process.

We examined if perturbation of KUZ fimction in Drosophila Schneider 2 (S2) cell cultures would affect NOTCH processing. S2 cells do not express any endogenous NOTCH protein (Fehon et al., 1990), but do express high levels of kuz mRNA. Upon transfection of a full-length N construct, the monoclonal antibody C17.9C6, which was raised against the intracellular domain of NOTCH, can detect fill length NOTCH (about 300 kd) and C-terminal fragments of about 100 kd (Fehon et al., 1990). We reasoned that if kuz is involved in generating this 100 kd species in S2 cells, then expression of KUZDN might interfere with this proteolytic event. Indeed, expression of KUZDN nearly abolished the 100 kd species in S2 cells, while the 300 kd species was not greatly affected, indicating that kuz is required for the NOTCH processing. Consistent with our results in transgenic flies that overexpression of full length KUZ did not perturb neurogenesis, transfection of a full length KUZ construct did not affect NOTCH processing in S2 cells.

Next, we performed similar experiments in developing imaginal discs. As described earlier, in transgenic flies containing KUZDN under the control of the heatshock promoter, one hour heatshock at the third instar larval stage resulted in extra bristles on the notum. The same heatshock regime also resulted in notches on the wing blade and extra photoreceptors in the eye. We followed the status of NOTCH processing in the wing and eye imaginal discs after the induction of KUZDN in these animals. As in transfected S2 cells, mAb C17.9C6 normally detects a 300 kd and a 100 kd NOTCH species in protein extracts of the third instar imaginal discs. After the induction of KUZDN by one hour heatshock, the 100 kd species gradually disappears; by 4 hours after induction, the 100 kd species is almost undetectable, while the 300 kd species has accumulated to a higher level. By 15 hrs after the heatshock, the 100 kd species is restored to wildtype levels presumably reflecting the decay of the KUZDN protein synthesized in response to the heatshock. The correlation between the reduction of the 100 kd species upon KUZDN expression and the resulting neurogenic phenotypes in imaginal tissues indicates the functional significance of the 100 kd NOTCH form detected in vivo.

Figure 2:
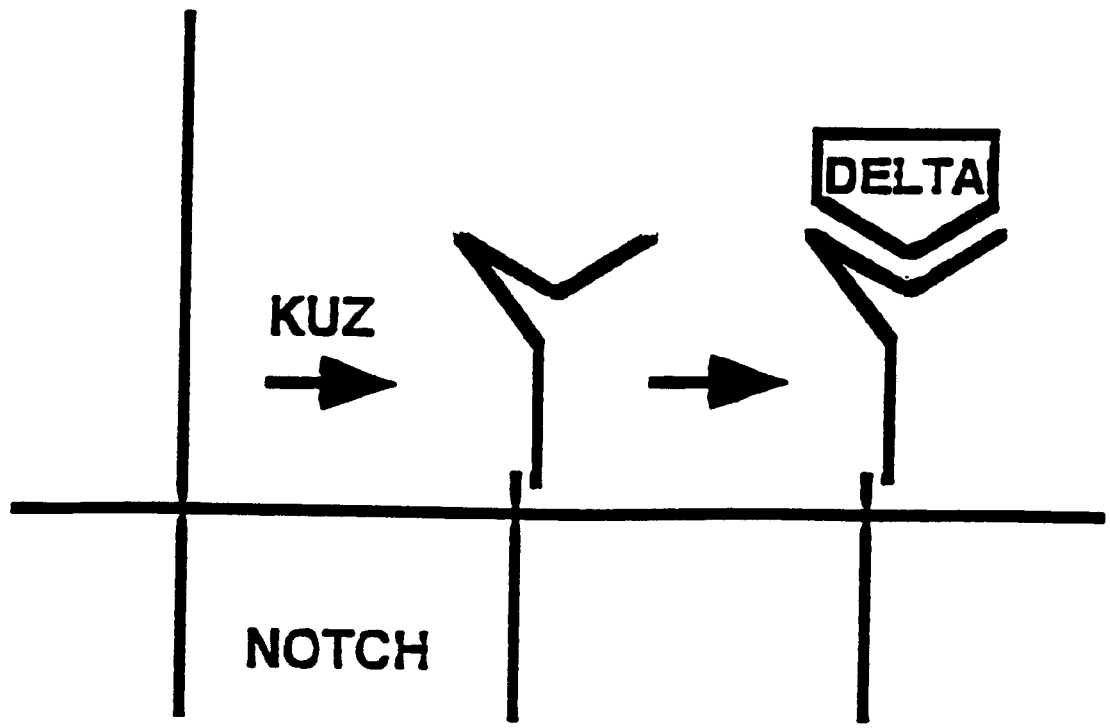
FIG. 2 shows a schematic of how KUZ protease can process NOTCH on the extracellular domain to generate an N-terminal extracellular fragment and the C-terminal 100 kd fragment containing the transmembrane and the cytoplasmic domain. These two fragments may remain tethered together to function as a competent NOTCH receptor, analogous to the maturation of the SEVENLESS receptor (Simon et al., 1989).

Finally, we examined NOTCH processing in kuz null mutant embryos. Since kuz is known to have a maternal contribution (supra), we generated germline clones to obtain embryos lacking all KUZ function. We found that while mAb C17.9C6 detects a 300 kd and a 100 kd species in wildtype embryos, only the 300 kd species is detected in kuz null embryos. This observation indicates that the phenotypes we generated by expression of KUZDN are not due to interference with genes other than kuz, such as other members of the ADAM family, and that kuz is required for the proteolytic processing of NOTCH (FIG. 2).

Our studies provide a general scheme for engineering dominant negative forms of ADAM proteins applicable to other ADAM genes. While all ADAMs possess a disintegrin-like and a metalloprotease-like domain, some ADAMs lack a consensus active site in the metalloprotease domain. These "protease dead" ADAMs resemble dominant negative forms of KUZ described herein and can function as endogenous inhibitors.

Experimental Procedures: Plasmid Constructs: We initially used the pGMR vector (Hay et al., 1994) to express full length KUZ and several N- and C- terminal deletion constructs in the eye. These constructs include 1, 2, 3, 4 and 7. Upon identification of 7 as a dominant negative form (KUZDN), we then used another expression vector pDMR to express constructs 1, 4, 5, 6, 7, 8 and 9. The pDMR vector utilizes the dpp disc specific enhancer to drive gene expression in multiple tissues including the wing and the notum. pDMR was constructed by the following steps. First, the heat shock responsive element in Casperhs (Pirotta, V. (1988). In Vectors: A Survey of Molecular Cloning Vectors and their Uses) was removed to yield Casperhs-1. A 4.3 kb dpp disc specific enhancer (Staehling-Hampton, K., et al. (1994). Cell Growth Differ. 5, 585–593) was inserted upstream of the hsp70 basal promoter in Casperhs-1 to yield pDMR (dpp mediated reporter). Construct 7 (KUZDN) was also cloned into pUAST (Brand and Perrimon, 1993) and pCasperhs to generate UAS/KUZDN and hs/KUZDN, respectively. A rough enhancer element (Heberlein et al., 1994) was then inserted into hs/KUZDN to generate rough/KUZDN. Constructs 1 (full length KUZ) and 7 (KUZDN) were also cloned downstream of the metallothionein promoter in pRMHa-3, a S2 cell expression vector (Bunch, T. A., et al. (1988) Nucl. Acids Res. 16, 1043–1061). The nucleotide coordinates of constructs 1 through 9 are as follows, using the same numbering as in GenBank accession no. U60591. 1 and 8: 723–5630; 2: 723–3578; 3: 723–3462; 4: 723–2757; 5: 1957–2757; 6: 1957–5630; 7 and 9: 2757–5630. Note that for all the N-terminal deletion constructs, a DNA fragment (nucleotides 723–940) containing the signal peptide was provided at the 5' end. Site directed mutagenesis was carried out using Stratagene's QuickChange system.

MKUZDN was generated by an N-terminal truncation that removes the pro and catalytic domains of MKUZ. The rest of MKUZ (nucleotide 1483–2573) was ligated either to a DNA fragment (723–940, according to nucleotide coordinates in U60591) containing the signal peptide of Drosophila KUZ to generate MKUZDN-1 or to a fragment (nucleotide 1-248) containing the signal peptide of MKUZ to generate MKUZDN-2. MKUZDN-1 was subcloned into pDMR and pUAST for overexpression in Drosophila, and MKUZDN-2 was subcloned into a modified CS2+vector (Turner, D. L. and Weintraub, H. (1994). Genes Dev. 8, 1434–1447.) for RNA injection in Xenopus embryos (see below).

Characterization of kuz Homologs from Mouse and Xenopus: PCR primers corresponding to sequences of a rat gene similar to kuz (GenBank accession: Z48444) were used to amplify a fragment from a mouse brain cDNA library. PCR product was then used to screen oligo(dT) and random primed cDNA libraries from the mouse PCC4 cell line (Stratagene). Two overlapping cDNA, mkuz2 and mkuz3 were characterized and sequenced, which together comprised the whole coding region. mkuz 2 extends from nucleotide 430 to 2573 and mkuz3 extends from 1 to 1345.

Xenopus kuz was cloned by PCR using degenerate primers (XK1) and (XK4) which correspond to Drosophila KUZ sequence HNFGSPHD (SEQ ID NO:2, residues 609–616) and GYCDVF, (SEQ ID NO:2, residues 870–875) respectively. First strand cDNA from stage 18 Xenopus embryos was used as template in a standard PCR reaction with an annealing temperature of 50° C. A PCR product of expected size was purified and used as template for another PCR reaction using a nested primer (XK3), corresponding to Drosophila KUZ sequence EECDCG, (SEQ ID NO:2, residues 688–693) and XK4. The PCR product was subcloned into Bluescript and sequenced. Anti-sense RNA was used as a probe for whole mount in situ hybridization of Xenopus embryos according to standard procedures (Harland, R. (1991). Meth. Cell Biol. 36, 685–695).

For RNA injections in Xenopus embryos, MKUZDN-2 was synthesized in vitro using SP6 RNA polymerase from a CS2+vector. Nuclear lacZ RNA was synthesized from plasmid pSP6 nucβGal. 500 pg of MKUZDN RNA, together with 100 pg of lacZ RNA was injected into one blastomere of Xenopus embryos at 2–4 cell stage. lacZ RNA was also injected alone as a control. Embryos were fixed at the neural plate stage and stained with Red-Gal (Research Organics, Inc.). Embryos were then processed for in situ hybridization with a neural specific β-tubulin probe.

Drosophila Genetics: For epistasis between kuz and Notch, an activated N construct containing only the cytoplasmic domain of NOTCH ($N^{act}$)under the control of the heatshock promoter (ITM3A insertion on the X chromosome, from Lieber, T., et al. (1993). Genes Dev. 7, 1949–1965) and a null kuz allele e29-4 (Rooke et al., 1996) were used. Flies of the genotype ITM3A/+; e29-4 ck FRT40A/+ were crossed to hsFlp/Y; FRT40 A. The progeny from such a cross were subjected to a one hr heatshock at 38° C. 24 to 48 hrs after egg laying to induce kuz mutant clones and another one hr heatshock at 7–9 hrs APF to induce the expression of $N^{act}$. Adult flies were processed for scanning electron microscopy and the clones identified by the cell autonomous ck epidermal hair marker as in Rooke et al. (1996).

kuz germline clones were generated as in Rooke et al. (1996). Females bearing germline clones were mated to e29-4/CyO males. kuz null embryos lacking both maternal and zygotic contribution can be distinguished from kuz maternal null embryos rescued with one zygotic copy of kuz at late embryonic stages since kuz null embryos fail to develop any cuticle while paternally rescued embryos develop some cuticle structures. kuz null embryos were hand-picked for making protein extracts.

Protein Extracts and Immunoblotting: About $2 \times 10^6$ S2 cells, 50 embryos, or imaginal discs from 16 third instar larvae were used for each extraction. These materials were homogenized and incubated for 20 min on ice in 90 µl of buffer containing 10 mM KCl, 20 mM Tris pH 7.5, 0.1% mercaptoethanol, 1 mM EDTA plus protease and phosphatase inhibitors (leupeptin, aprotinin, PMSF and sodium vanadate). Supernatant was collected after a low speed spin of 2000 rpm for 5 min. 12 µl of supernatant was run on a 6% SDS polyacrylamide gel. Blotting, antibody incubation, and chemiluminescent detection using the ECL kit were as described in Fehon et al. (1990).

What is claimed:

1. An isolated polynucleotide encoding a polypeptide comprising an amino acid sequence selected from the group consisting of residues 320–673 of SEQ ID NO:2, residues 212–454 of SEQ ID NO:4, SEQ ID NO:6, and residues 213–455 of SEQ ID NO:8.

2. A polynucleotide according to claim 1, wherein the amino acid sequence is residues 320–673 of SEQ ID NO:2.

3. A polynucleotide according to claim 1, wherein the amino acid sequence is residues 212–454 of SEQ ID NO:4.

4. A polynucleotide according to claim 1, wherein the amino acid sequence is SEQ ID NO:6.

5. A polynucleotide according to claim 1, wherein the amino acid sequence is residues 213–455 of SEQ ID NO:8.

6. A polynucleotide according to claim 1, wherein the amino acid sequence is SEQ ID NO:2.

7. A polynucleotide according to claim 1, wherein the amino acid sequence is SEQ ID NO:4.

8. A polynucleotide according to claim 1, wherein the amino acid sequence is SEQ ID NO:8.

9. A method of making a polypeptide, comprising the following steps: incubating a host cell or cellular extract containing a polynucleotide according to claim 1 under conditions whereby the polypeptide encoded by the polynucleotide is expressed and recovering the expressed polypeptide.

10. An isolated polynucleotide encoding a dominant-negative mutant of a KUZ polypeptide, said mutant comprising (a) an amino acid sequence selected from the group consisting of SEQ ID NO:2, 4 and 6, wherein the protease domain is deleted, or (b) SEQ ID NO:2, wherein glutamate at residue 606 is substituted with alanine.

11. A method for modulating Notch signal transduction pathway in a cell comprising transforming the cell with a polynucleotide according to claim 1 whereby Notch signal transduction is modulated.

12. A vector comprising a polynucleotide according to claim 1.

13. An expression vector comprising a polynucleotide according to claim 1 operably linked to a promoters.

14. A cell comprising a vector according to claim 13.

* * * * *